US00RE46276E

(19) United States
(12) Reissued Patent
Hardem et al.

(10) Patent Number: US RE46,276 E
(45) Date of Reissued Patent: Jan. 17, 2017

(54) TRIAZOLO(4,5-D)PYRIMIDINE COMPOUNDS

(71) Applicant: AstraZeneca UK Limited, London (GB)

(72) Inventors: David Hardem, Sutton Bonington (GB); Anthony Ingall, Minehead (GB); Brian Springthorpe, Stanford on Soar (GB); Paul Willis, Geneva (CH); Simon Guile, Hathern (GB)

(73) Assignee: AstraZeneca UK Limited, London (GB)

(21) Appl. No.: 14/976,977

(22) Filed: Dec. 21, 2015

Related U.S. Patent Documents

Reissue of:
(64) Patent No.: 6,525,060
Issued: Feb. 25, 2003
Appl. No.: 09/508,195
PCT Filed: Dec. 2, 1999
PCT No.: PCT/SE99/02256
§ 371 (c)(1),
(2) Date: Mar. 8, 2000
PCT Pub. No.: WO00/34283
PCT Pub. Date: Jun. 15, 2000

(30) Foreign Application Priority Data

Dec. 4, 1998 (SE) ..... 9804211
Apr. 9, 1999 (SE) ..... 9901271

(51) Int. Cl.

| | |
|---|---|
| ***C07D 239/00*** | (2006.01) |
| ***A61K 31/519*** | (2006.01) |
| ***A61P 9/00*** | (2006.01) |
| ***A61P 9/10*** | (2006.01) |
| ***C07D 239/48*** | (2006.01) |
| ***C07D 487/04*** | (2006.01) |
| ***C07D 487/00*** | (2006.01) |
| ***C07C 211/40*** | (2006.01) |

(52) U.S. Cl.
CPC ..... *C07D 487/04* (2013.01); *A61K 31/519* (2013.01); *C07C 211/40* (2013.01); *C07D 239/48* (2013.01)

(58) Field of Classification Search
None
See application file for complete search history.

(56) References Cited

U.S. PATENT DOCUMENTS

| | | | | |
|---|---|---|---|---|
| 3,106,578 | A | 10/1963 | Kaiser et al. | |
| 3,509,129 | A | 4/1970 | Kampe et al. | |
| 3,590,029 | A | 6/1971 | Koch et al. | |
| 4,016,204 | A | 4/1977 | Rajadhyaksha | |
| 4,543,255 | A | 9/1985 | Shealy et al. | |
| 4,742,064 | A | 5/1988 | Vince | |
| 5,288,726 | A | 2/1994 | Koike et al. | |
| 5,338,725 | A | 8/1994 | Ojima et al. | |
| 5,620,676 | A | 4/1997 | Jacobson et al. | 514/263 |
| 5,631,259 | A | 5/1997 | Jahne et al. | |
| 5,652,366 | A | 7/1997 | Spada et al. | |
| 5,688,774 | A | 11/1997 | Jacobson et al. | |
| 5,747,496 | A | 5/1998 | Cox et al. | |
| 5,817,660 | A | 10/1998 | Borcherding et al. | |
| 5,831,099 | A | 11/1998 | Dave et al. | |
| 5,948,437 | A | 9/1999 | Parikh et al. | |
| 5,997,089 | A | 12/1999 | Kawasaki | |
| 6,156,756 | A | 12/2000 | Hardern et al. | |
| 6,251,910 | B1 | 6/2001 | Guile et al. | 514/258 |
| 6,559,143 | B1 | 5/2003 | Bjore et al. | |
| 6,605,600 | B1 | 8/2003 | Ensinger et al. | |
| 6,974,868 | B2 | 12/2005 | Hardern et al. | |
| 7,250,419 | B2 | 7/2007 | Hardern et al. | |
| 7,265,124 | B2 | 9/2007 | Bohlin et al. | |
| 8,425,934 | B2 | 4/2013 | Banks | |
| 9,056,838 | B2 | 6/2015 | Kansal et al. | |
| 9,359,366 | B2 | 6/2016 | Sun et al. | |
| 2003/0165563 | A1 | 9/2003 | Murphy et al. | |
| 2007/0265282 | A1 | 11/2007 | Hardern et al. | |
| 2008/0214812 | A1 | 9/2008 | Hardern et al. | |
| 2010/0069408 | A1 | 3/2010 | Hardern et al. | |
| 2012/0165348 | A1 | 6/2012 | Hardern et al. | |
| 2013/0072503 | A1 | 3/2013 | Hardern et al. | |

(Continued)

FOREIGN PATENT DOCUMENTS

| | | |
|---|---|---|
| CA | 994773 A | 8/1976 |
| EP | 0 521 463 A2 | 1/1993 |

(Continued)

OTHER PUBLICATIONS

Paragraph IV Certification Letter #1, dated Oct. 1, 2015, pp. 1-34.
Paragraph IV Certification Letter #2, dated Sep. 23, 2015, pp. 1-50.
Paragraph IV Certification Letter #3, dated Sep. 18, 2015, pp. 1-72.
Paragraph IV Certification Letter #4, dated Sep. 17, 2015, pp. 1-145.
Paragraph IV Certification Letter #5, dated Oct. 5, 2015, pp. 1-67.
Paragraph IV Certification Letter #6, dated Oct. 3, 2015, pp. 1-58 and Appendix pp. 1-8.
Daly et al., Structure-Activity Relationships for N6-Substituted Adenosines at a Brain A1-Adenosine Receptor with a Comparison to an A2-Adenosine Receptor Regulating Coronary Blood Flow, Biochemical Pharmacology 35:2467-81 (1986).

(Continued)

*Primary Examiner* — Alan Diamond

(57) ABSTRACT

Triazolo[4,5-d]pyrimidine compounds, their use as medicaments, compositions containing them and processes for their preparation. The compounds of the invention have the formula (I) as follows:

(I)

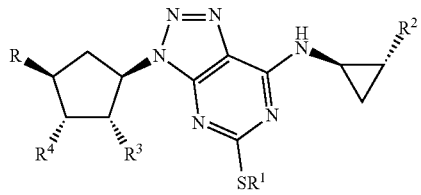

wherein R, X and $R^1$ through $R^3$ are as defined in the specification.

23 Claims, No Drawings

(56) References Cited

U.S. PATENT DOCUMENTS

| | | | |
|---|---|---|---|
| 2013/0109702 | A1 | 5/2013 | Hardern et al. |
| 2014/0296258 | A1 | 10/2014 | Hardern et al. |
| 2015/0073146 | A1 | 3/2015 | Dahanukar et al. |
| 2015/0152111 | A1 | 6/2015 | Hardern et al. |

FOREIGN PATENT DOCUMENTS

| | | | |
|---|---|---|---|
| EP | 1 063 231 | A1 | 12/2000 |
| EP | 0 864 572 | B2 | 4/2001 |
| GB | 1 561 725 | | 2/1980 |
| GB | 2 217 320 | A2 | 10/1989 |
| KR | 10-053837 | | 3/2001 |
| RU | 2 114 846 | C1 | 7/1998 |
| WO | 01/92262 | | 6/1990 |
| WO | 91/07405 | | 5/1991 |
| WO | 92/12718 | A1 | 8/1992 |
| WO | 92/17488 | | 10/1992 |
| WO | 94/17803 | | 8/1994 |
| WO | 94/18216 | | 8/1994 |
| WO | 99/31100 | | 6/1996 |
| WO | 96/29345 | | 9/1996 |
| WO | 96/40686 | | 12/1996 |
| WO | 90/06671 | | 1/1997 |
| WO | 97/03084 | | 1/1997 |
| WO | 97/19170 | | 5/1997 |
| WO | 98/28300 | | 7/1998 |
| WO | 98/28300 | A1 | 7/1998 |
| WO | 99/05142 | | 2/1999 |
| WO | 99/05143 | | 2/1999 |
| WO | 0128992 | | 4/2001 |
| WO | 97/03084 | | 12/2001 |
| WO | 03/030800 | | 4/2003 |
| WO | 2010/030224 | A1 | 3/2010 |
| WO | 2011/101740 | A2 | 8/2011 |
| WO | 2012/001531 | A2 | 1/2012 |
| WO | 2012/085665 | A2 | 6/2012 |
| WO | 2012/172426 | A1 | 12/2012 |
| WO | 2013/079589 | A1 | 6/2013 |
| WO | 2013/150495 | A2 | 10/2013 |
| WO | 2014/102830 | A1 | 3/2014 |
| WO | 2014/083139 | A1 | 6/2014 |
| WO | 2014/118808 | A2 | 8/2014 |
| WO | 2014/195861 | A2 | 11/2014 |
| WO | 2016/001851 | A2 | 1/2016 |
| WO | 2016/120729 | A1 | 8/2016 |
| ZA | 98/6050 | | 7/1998 |

OTHER PUBLICATIONS

Tompkinson et al., P2T Purinoceptor Antagonists. A QSAR Study of Some 2-Substituted ATP Analogues, J. Pharm. Pharmacol. 48:206-209 (1996).
The Practice of Medicinal Chemistry (Camille G. Wermuth, 1st ed.), pp. 617, 631, 636 (1996).
Albert, Chemistry of 8-Azapurines (1,2,3-Triazolo[4,5-d]pyrimidines), Advances in Heterocyclic Chemistry, 39:117-180 (1986).
Santi et al., 5-Fluoro-2'-Deoxyuridylate: Covalent Complex with Thymidylate Synthetase, Proc. Nat. Acad. Sci. 69:1855-1857 (1972).
Heidelberger et al., Fluorinated Pyrimidines and Their Nucleosides, Adv. Enzymol. And Related Areas of Mol. Bio., 54:57-119 (1983).
Santi, Perspectives on the Design and Biochemical Pharmacology of Inhibitors of Thymidylate Synthetase, J. Med. Chem. 23:103-111 (1980).
Lewis et al., Topics in Molecular Pharmacology (Burgen, A. S. V., & Roberts, G. C. K., Eds.) 1:169-219 (1981).
Connick et al., Fluorine-19 Nuclear Magnetic Resonance Studies of Binary and Ternary Complexes of Thymidylate Synthase Utilizing a Fluorine-Labeled Folate Analogue, Biochem 32:9888-9895 (1993).
Jacobson et al., Search for New Purine-and Ribose-Modified Adenosine Analogues as Selective Agonists and Antagonists at Adenosine Receptors, J. Med. Chem. 38:1174-1188 (1995).
Melandri et al., Benefit of Adding Low Molecular Weight Heparin to the Conventional Treatment of Stable Angina Pectoris A Double-Blind, Randomized, Placebo-Controlled Trial, Circulation 88:2517-2523 (1993).
Pivia et al., Introduction to Oraganic Laboratory Techniques, 2d Ed. (1982).
Aukland et al., Platelet inhibition with Ticlopidine in atherosclerotic intermittent claudication, J. Clin. Pathol. 35:740-743 (1982).
Haleblain et al., Pharmaceutical Applications of Polymorphism, J. of Pharmaceutical Sciences, vol. 58, No. 8, 911-929 (1969).
Bruger's Medicinal Chemistry, Fourth Edition, pp. 58-59 (1980).
Clopidogrel (PLAVIX) FDA Label (2010).
Haleblian et al., Pharmaceutical Applications of Polymorphism, J. of Pharmacutical Sci., vol. 58, No. 8 (1969).
McCrone, Polymorphism, Chapter 8 in Physics and Chemistry of the Organic Solid State (1965).
1987 FDA Guideline for Submitting and Supporting Documentation in Drug Applications for the Manufacture of Drug Substances.
ICH Harmonised Tripatite Guideline, Specifications: Test Procedures and Acceptance Criteria for New Drug Substances and New Drug Products: Chemical Substances Q6A (1999).
FDA Q6A Specifications: Test Procedures and Acceptance Criteria for New Drug Substances and New Drug Products: Chemical Substances (2000).
Borka, Crystal Polymorphism of Pharmaceuticals, Acta. Pharm. Jugosl. 40:71-94 (1990).
Trelfall, Analysis of Organic Polymorphs A Review, Analyst V. 120 (1995).
Bryn et al., Pharmaceutical Solids: A Strategic Approach to Regulatory Considerations, Pharmacutical Research vol. 12, No. 7 (1995).
Caira, Crystalline Polymorphism of Organic Compounds, Top. Curr. Chem. 198:163-208 (1998).
Byrn et al., Solid State Chemistry of Drugs, 2d ed., pp. 266-278 (1999).
Yu et al., Physical Characterization of Polymorphic Drugs: An Integrated Characterized Strategy, PSTT 1:118-127 (1998).
Berstein, Polymorphism in Molecular Crystals (2002), p. 252.
Guilllory, Generation of Polymorphs, Hydrates, Solvates, and Amorphous Solids, chapter in Polymorphism in Pharmaceutical Solids, 183-226 (1999).
Weissbuch et al., Molecular Recognition at Crystal Interface, Science 253:637-645 (1991).
Weissbuch et al., Understanding and Control of Nucleation, Habit, Dissolution and Structure of Two- and Three-Dimensional Crystals Using 'Tailor-Made' Auxiliaries, Acta Cryst. B51:115-148 (1995).
Weiser, Postmytocardinal Infraction Syndrome, Circulation 20:371-380 (1951).
Hanawalt, Chemical Analysis of X-Ray Diffraction, Powder Diffraction vol. 1 No. 2 pp. 2-14 (1986).
Mar. 27, 2015 Korean Appeal For Judgment against Korean Patent No. 724,924; Claimant: Daewon Pharmaceutical Co.
Mar. 27, 2015 Korean Appeal For Judgment against Korean Patent No. 724,924; Claimant: JW Pharmaceutical Corp.
Mar. 30, 2015 Korean Appeal For Judgment against Korean Patent No. 724,924; Claimant: Kukje Pharma Ind. Co., Ltd.
Mar. 27, 2015 Korean Appeal For Judgment against Korean Patent No. 724,924; Claimant: Daewoong Pharmacutical Co.
Mar. 27, 2015 Korean Appeal For Judgment against Korean Patent No. 724,924; Claimant: Bio and Chemical R&D.
Nov. 24, 2015 Revocation Petition by Micro Labs Ltd. against Indian Patent No. 209907.
Awni et al., The Effect of Mild or Moderate Hepatic Impairment (Cirrhosis) on the Pharmacokinetics of Zileuton, Clin. Pharacokinet 29 (Suppl. 2): 49-61 (1995).
Chapman et al, Difluoramination of Heterocyclic Ketones: Control of Microbasicity, Journal of Organic Chemistry 63(5), pp. 1566-1570 (1998).
Chapman et al, Nitrolysis of a Highly Deactivated Amide by Protonitronium, Synthesis and Structure of HNFX, Journal of Organic Chemistry 64(3), pp. 960-965 (1999).

(56) References Cited

OTHER PUBLICATIONS

Dave et al, Facile Preparation of 3,7-Diazabicyclo[3.3.0]octane and 3,7,10-Triheterocyclic [3.3.3]Propellane Ring Systems from 1,5-Diazacyclooctane 3,7-Derivatives, Journal of Organic Chemistry 61(25), pp. 8897-8903 (1996).
Dorwald F.A., Side Reactions in Organic Synthesis, Wiley: VCH, Weinheim p. IX of Preface (2005).
Jin et al., Molecular Basis for ADP-induced Platelet Activation, The Journal of Biological Chemistry, vol. 273, No. 4, pp. 2030-2034(1998).
Mistry et al., Glucuronidation In Vitro and In Vivo Comparison of Intestinal and Hepatic Conjugation of Morphine, Naloxone, and Buprenorphine; The American Society for Pharmacology and Experimental Therapeutics, vol. 15, No. 5; pp. 710-717 (1987).
Paudler et al., 1,5-Bis(p-toluenesulfonyl)-3,7-Dihydroxyoctahydro-1,5-diazocine, Journal of Organic Chemistry, 31(1), pp. 277-280 (1966).
Paudler et al., 3,7-Disubstituted octahydro-1,5-diazocines. Their conversion into tetrahydro-1,5-diazocines and to ring-contracted products, Journal of Organic Chemistry; 32(8), pp. 2425-2430 (1967).
Puri et al., Modulation of Platelet Responses by 2-[3-(Bromo-2-oxopropylthio)]-adenosine . . . , Archives of Biochemistry and Biophysics, vol. 343, No. 1, pp. 140-145 (1997).
Rodrigues, Commentary, Use of In Vitro Human Metabolism Studies in Drug Development, Biochemical Pharmacology, vol. 48, No. 12, pp. 2147-2156 (1994).
Stetter, Synthese des 1.3-Diaza-6-oxa-adamantans, Chemische Berichte, 96(11), pp. 2827-2830 (1963).
Villgarda et al., trans-2-Aryl-N,N-dipropylcyclopropylamines: Synthesis and Interactions with 5-HT1A Receptors, Journal of Medical Chemistry; vol. 39, No. 7; pp. 1485-1493 (1996); SP002262871.
Vippagunta et al., Advanced Drug Delivery Reviews, 48; pp. 3-26 (2001).
Supplemental Paragraph IV Certification Letter #3, dated Jul. 27, 2016, pp. 1-42.
Defendant Watson Laboratories, Inc.'s Answer to Complaint, Defenses, and Counterclaims in *AstraZeneca, LP* v. *Watson Laboratories, Inc.*, Civil Action No. 1:16-338-RGA.
Defendants' Initial Invalidity and Uneforceability Contentions in Civil Action No. 15-1000-RGA (dated Jun. 24, 2016).
Berstein, Conformational Polymorphism, in Organic Solid State Chemistry 471-518 (G. R. Desiraju ed., 1987).
Bhagwat et al., P2 Purine and Pyrimidine Receptors: Emerging Superfamilies of G-Protein-Coupled and Ligand-Gated Ion Channel Receptors, Eur. J. Med. Chem., 32:183-193 (1997).
Brittain, Preface to Polymorphism in Pharmaceutical Solids, Drugs and Pharmaceutical Studies, 95:iii-v (H. G. Brittain, ed., 1999).
Brittain et al., Effects of Pharmaceutical Processing on Drug Polymorphs and Solvates, in Polymorphism in Pharmaceutical Solids 331-361 (H. G. Brittain ed., 1999).
Cusack et al., Effects of Phosphate-Modified Analogs of Adenosine 5'-Diphosphate and Adenosine 5'-Triphosphate At P2T-Purinoreceptors Mediating Human Platelet Activation by ADP, Drug Dev. Res. 37:212-222 (1996).
Filler, Fluorinated Compounds of Medicinal Interest, ChemTech Dec. (1974).
Filler et al., Fluorine in Biomedicinal Chemistry: An Overview of Recent Advances and Selected Topics, Biomedicinal Aspects of Fluorine Chemistry 1-32 (R. Filler and Y. Kobayashi eds., 1982).
Filler, Biologically-Active Fluorochemicals, J. Fluorine Chemistry 33:361-375 (1986).
Haleblian et al., Pharmaceutical Applications of Polymorphism, J. Pharm. Sci. 58(8):911-929 (1969).
Humphries et al., FPL 66096: A Novel, Highly Potent and Selective Antagonist at Human Platelet P2T-Purinoceptors, Br. J. Pharmacol. 113:1057-1063 (1994).
Humphries et al., Pharmacological Profile of the Novel P2T-Purinoceptor Antagonist, FPL 67085 in vitro and in the Anesthetized Rat in vivo, Br. J. Pharmacol. 115:1110-1116 (1995).
Humphries et al., A Novel Series of P2T Purinoceptor Antagonists: Definition of the Role of ADP in Arterial Thrombosis, TiPS 16:179-181 (1995).
Nassim et al., The Short-Acting P2T-Purinoceptor Antagonist, FPL 67085, Reliably, Reversibly, and Safely Inhibits ADP-Induced Platelet Aggregation ex vivo in Man, Br. J. Clin. Pharmacol. 39(1):98P (1995).
O'Hagan et al., Some Influences of Fluorine in Bioorganic Chemistry, Chem. Commun. 645-652 (1997).
Park et al., Effects of Fluorine Substitution on Drug Metabolism: Pharmacological and Toxicological Implications, Drug Metab. Rev. 26(3):605-643 (1994).
Raw et al., Regulatory Considerations of Pharmaceutical Solid Polymorphism in Abbreviated New Drug Applications (ANDAs), Adv. Drug. Deliv. Rev. 56:397-414 (2004).
Siddiqui et al., Search for New Purine- and Ribose-Modified Adenosine Analogues as Selective Agonists and Antagonists at Adenosine Receptors, J. Med. Chem. 38:1174-1188 (1995).
Pavia et al., Introduction to Organic Laboratory Techniques, 2nd Ed., 481-491 (1982).
Threlfall, Analysis of Organic Polymorphs, A Review, Analyst 120:2435-2460 (1995).
FDA Center for Drug Evaluation and Research,Guideline for Submitting Supporting Documentation in Drug Applications for the Manufacture of Drug Substances (1987).
ICH Harmonized Tripartite Guideline, Specifications: Test Procedures and Acceptance Criteria for New Drug Substances and New Drug Products: Chemical Substances, Q6A (1999).
A Guide to IUPAC Nomenclature of Organic Compounds Recommendations 1993, 149-155 (R. Panico et al. eds., 1993).
Jacobson et al., Structure-Activity Relationships of 9-Alkyladenine and Ribose-Modified Adenosine Derivatives at Rat A3 Adenosine Receptors, J Med. Chem. 38:1720-1735 (1995).
Koomen, Synthesis and Biological Properties of Selected Nucleoside Analogues, Recl. Tray. Chim. Pays-Bas 112:51-65 (1993).
Patani et al., Bioisosterism: A Rational Approach in Drug Design, Chem. Rev. 96:3147-3176 (1996).
Balzarini et al., Human Immunodeficiency Virus Type 1 Drug-Resistance Patterns with Different 1[(2-Hydroxyethoxy) methyl]-6-(phenylthio)thymine Derivatives, Mol. Pharmacology 44:694-701 (1993).
Chlud, Zur Anwendung von NSAR-Topika bei irritierten and dekompensierten Arthrosen, Wiener Medizinische Wochenschrift 149(19/20):546-547 (1999).
Elion et al., Selectivity of Action of an Antiherpetic Agent, 9-(2-hydroxyethoxymethyl)guanine, Proc. Natl. Acad. Sci., 74 (12):5716-5720 (1977).
Chemical Abstracts Index Guide, Appendix IV, ¶¶202-203 (1997).
Radebaugh et al., Preformulation, from The Science and Pharmacy, Chapter 38, (1995).
Byrn et al., Pharmaceutical Solids: A Strategic Approach to Regulatory Considerations, Pharmaceutical Research, 12 (7):945-954 (1995).
Begstrom et al., Fluorine Substituted Analogs of Nucleic Acid Components, in Fluorine-Containing Molecules: Structure, Reactivity, Synthesis, and Applications 259-308 (J. F. Liebman et al. eds., 1988).
Jun. 4, 2016 Counter Statement by Respondent AstraZeneca AB in response to Revocation Petition by Micro Labs Ltd. against Indian Patent No. 209907.
Springthorpe et al., From ATP to AZD6140: The discovery of an orally active reversible P2Y12 receptor antagonist for the prevention of thrombosis, Bioorg Med Chem Lett. 17(21):6013-8 (2007).
van Giezen et al., Preclinical and clinical studies with selective reversible direct P2Y12 antagonists, Semin. Thromb. Hemost. 31(2):195-204 (2005).
Tantry et al., AZD6140, Expert Opin. Investig. Drugs 16(2):225-9 (2007).
Van de Werf, Dual antiplatelet therapy in high-risk patients, Eur. Heart J. 9(supp D):D3-9 (2007).

(56) References Cited

OTHER PUBLICATIONS

Bode et al., The use of antiplatelet agents following percutaneous coronary intervention: focus on late stent thrombosis, Eur. Heart J. 9 (supp D):D10-19 (2007).
Husted, New developments in oral antiplatelet therapy, Eur. Heart J. 9 (suppl D) D:20-7 (2007).
Owen et al., AZD6140. Antiplatelet therapy P2Y12 (P2T) receptor antagonist., Drugs Fut. 32(10):845-53 (2007).
Bassand, Unmet needs in antiplatelet therapy, Eur. Heart. J. 10(supp D):D3-11 (2008).
Becker, Emerging constructs to maintain safety among patients with acute coronary syndromes requiring surgical coronary revascularization, Eur. Heart J. 10(supp D):D12-22 (2008).
van Giezen, Optimizing platelet inhibition, Eur. Heart J. 10(supp D):D23-9 (2008).
Storey, New developments in antiplatelet therapy, Eur. Heart J. 10(supp D):D30-7 (2008).
Wallentin, Dual antiplatelet therapy in the drug-eluting stent era, Eur Heart J. 10(supp D): D38-44 (2008).
Husted, Unmet needs in oral antiplatelet therapy with ADP receptor blocking agents, Fundam. Clin. Pharmacol. 23 (1):1-9 (2009).
Husted et al., Ticagrelor: The first reversibly binding oral P2Y12 receptor antagonist, Cardiovasc. Ther. 27(4):259-74 (2009).
Becker et al., Platelet P2Y12 receptor antagonist pharmacokinetics and pharmacodynamics: a foundation for distinguishing mechanisms of bleeding and anticipated risk for platelet-directed therapies, Thromb. Haemost. 103 (3):535-44 (2010).
Warner et al., Anti-platelet therapy: cyclooxygenase inhibition and the use of aspirin with particular regard to dual anti-platelet therapy, Br. J. Clin. Pharmacol. 72(4):619-33 (2011).
Deeks, Ticagrelor: A review of its use in the management of acute coronary syndromes, Drugs 71(7):909-33 (2011).
Husted, Evaluating the risk—benefit profile of the direct-acting P2Y12 inhibitor ticagrelor in acute coronary syndromes, Postgrad. Med. 123(6):79-90 (2011).
Berger et al., Is there an association between aspirin dosing and cardiac and bleeding events after treatment of acute coronary syndrome? A Systematic Review of the Literature., Am. Heart J. 164(2):153-62 (2012).
Angiolillo, The evolution of antiplatelet therapy in the treatment of acute coronary syndromes: from aspirin to the present day, Drugs. 72(16):2087-116 (2012).
Tantry et al., Influence of genetic polymorphisms on platelet function, response to antiplatelet drugs and clinical outcomes in patients with coronary artery disease, Expert Rev. Cardiovasc. Ther. 11(4):447-62 (2013).
Carroll et al., Statistical evaluation and analysis of regional interactions: The Plato trial case study, Stat. Biopharm. Res. 5(2):102-4 (2013).
Berger, Aspirin, Clopidogrel, and Ticagrelor in Acute Coronary Syndromes, Am. J. Cardiol. 112(5):737-45 (2013).
Foody, Antiplatelet Therapy in Women with Acute Coronary Syndrome, J. of Family Practice, 63(2 Supp):S3-8 (2014).
Tiwari et al., Risk factors for cardiovascular events and bleeding complications following non-cardiac surgery or procedure in patients with drug eluting stent placement, Heart Asia. 6:69-75 (2014).
Cattaneo et al., Adenosine-mediated effects of ticagrelor: evidence and potential clinical relevance, J. Am. Coll. Cardiol. 63(23):2503-9 (2014).
Dobesh et al., Ticagrelor: Pharmacokinetics, Pharmacodynamics, Clinical Efficacy, and Safety, Pharmacotherapy, 34 (10):1077-90 (2014).
Vengoechea, Management of acute coronary syndrome in the hospital: a focus on ACCF/AHA guideline updates to oral antiplatelet therapy, Hospital Practice. Aug. 42(3):33-47 (2014).
Price et al., A randomised trial of the pharmacodynamic and pharmacokinetic effects of ticagrelor compared with clopidogrel in Hispanic patients with stable coronary artery disease, J. Thromb. Thrombolysis. 39(1):8-14 (2015).
Clark et al., Managing the acute coronary syndrome patient: Evidence based recommendations for anti-platelet therapy, Heart & Lung. 44(2):141-9 (2015).
Roffman, Developments in Oral Antiplatelet Agents for the Treatment of Acute Coronary Syndromes, J. of Pharmacy Practice (2015).
Cayla et al., Updates and Current Recommendations for the Management of Patients With Non-ST-Elevation Acute Coronary Syndromes: What It Means for Clinical Practice, Am. J. Cardiol. 115(5 Supp):10A-22A (2015).
Huo et al., Challenges and solutions in medically managed ACS in the Asia-Pacific region: Expert recommendations from the Asia-Pacific ACS Medical Management Working Group, Int. J. Cardiol. 183:63-75 (2015).
Humphries et al., "Daring to be Different": The Discovery of Ticagrelor, The Handbook of Medicinal Chemistry, Principals and Practice (2015).
Guile, Chemical Abstracts, vol. 130, 168386 (1999).
Sherry-McKenna, et al., Monoamine oxidase inhibitors: effects on tryptophan concentrations in rat brain, J. Neural. Transm. (Supp) 41:155-163 (1994).
Jung et al., Total Synthesis of Neplanocin A., Helvetica Chimica Acta, vol. 66, No. 7, pp. 1915-1921 (1983).
3721-26-4 Registry, Cyclopropanamine, 2-phenyl-, (1R-trans)-Cyclopropylamine, 2-phenyl-, trans-(-)- Entered STN: Nov. 16, 1984, (see also 13531-35-6 Registry and 69684-89-5 Registry for other stereo isomers) 69684-89-5 Registry, Cyclopropanamine, 2-(3-chlorophenyl)-, hydrochloride, trans-, Entered STN: Feb. 8, 1991.
Wermuth, The Practice of Medicinal Chemistry, Academic Press Inc., p. 182-185, 226-228 and 346-348 (1996).
Paragraph IV Certification Letter #7, dated May 4, 2016.
Jun. 16, 2015 Revocation Petition by Micro Labs Ltd. against Indian Patent No. 247984.
Bryn et al., Solid-State Chemistry of Drugs, 2d ed., pp. 490-492 (1999).
AstraZeneca's Proposed Construction of Claim Terms and Intrinsic and Extrinsic Support, Cons. Civil Action No. 15-1000-RGA (Sep. 1, 2016).
Defendants' Initial Proposed Claim Constructions, Cons. Civil Action No. 15-1000-RGA (Sep. 1, 2016).
Proposed Construction of Claim Terms and Intrinsic and Extrinsic Support, Cons. Civil Action No. 15-1000-RGA (Sep. 26, 2016).
Defendants' Preliminary Identification of Evidence to Rebut Plaintiffs' Proposed Claim Constructions, Cons. Civil Action No. 15-1000-RGA (Sep. 26, 2016).
Fox et al., Nomenclature of Organic Compounds, 2d ed., Chapter 30, "Stereoisomers" (2001).
Print out from http:/webbok.nist.gov/cgi/cbook.cgi?ID=87694 for "(R,R)-Tartaric acid".
F. Carey, A Brief History of Systematic Organic Nomenclature, from Organic Chemistry, Fourth Edition, p. 63 (2000).
Naming and Indexing of Chemical Substances for Chemical Abstracts 2007 Edition (Chemical Abstract Service, 2008), p. 1.
Weisgerber, Chemical Abstracts Service Chemical Registry System: History, Scope, and Impacts, J. of the American Soc. for Info. Sci. 48(4):349-360 (1997).
Rules of Carbohydrate Nomenclature, J. of Organic Chem., 28(2):281-291 (1963).
Chambers Science and Technology Dictionary, p. 24 (1988).
Grant & Hackh's Chemical Dictionary, 5th ed., p. 24 (1987).
McGraw-Hill Dictionary of Scientific and Technical Terms, 6th ed., p. 68 (2003).
Alberts et al., Molecular Biology of the Cell, 4th ed., p. G:2 (2002).
Jones et al., Chemistry—Molecules, Matter, and Change, 4th ed., p. B2 (2000).
Webster's Ninth New Collegiate Dictionary, p. 70 (1986).
Blackwood et al., Chemical Abstracts Stereochemical Nomenclature of Organic Substances in Ninth Collective Period (1972-1976), J. of Chem. Info. and Comput. Sci., 15(2):67-72 (1975).
Blackwood et al., Chemical Abstracts Service Chemical Registry System. 13. Enhanced Handling of Stereochemistry, J. of Chem. Info. and Comput. Sci., 31(2):204-212 (1991).

(56) References Cited

OTHER PUBLICATIONS

Thurlow, Chemical Nomenclature, pp. 83-84 (1998).
Agatonovic-Kustrin et al., Powder Diffractomertic Assay of Two Polymorphic Forms of Ranitidine Hydrochloride, Int. J. of Pharmaceutics, 184:107-114 (1999).
Beck et al., A New Family of Mesoporous Molecular Sieves Prepared with Liquid Crystal Templates, J. Am. Chem. Soc., 114:10834-10843 (1992).
Brittain, Polymorphism in Pharmaceutical Solids, pp. 227-278 (1999).
Elements of X-ray Diffraction, Second Edition (Ed. Cullity), pp. 397-420 (1978).
Introduction to X-ray Powder Diffractometry (Eds. Jenkins and Snyder), pp. 261-286 (1996).
Introduction to X-ray Powder Diffractometry (Eds. Jenkins and Snyder), pp. 319-353 (1996).
United States Pharmacopeia USP 24, NF 19 <941> "X-Ray Diffraction", pp. 2005-2007 (2000).
Vartuli et al., Effect of Surfactant/Silica Molar Ratios on the Formation of Mesoporous Molecular Sieves: Inorganic Mimicry of Surfactant Liquid-Crystal Phases and Mechanistic Implications, Chem. Mater. 6:2317-2326 (1994).
Naming and Indexing of Chemical Substances for Chemical Abstracts 2007 Edition (2008), pp. 1-154.
Sorrell, Organic Chemistry, pp. 52-55 (1999).
Morrison et al., Organic Chemistry, 3d ed., pp. 79-83 (1973).
Mosby's Medical Dictionary, revised 2d ed., p. 40 (1987).
Bernstein, Polymorphism in Molecular Crystals, pp. 111, 117 (2002).
Bryn et al., Solid-State Chemistry of Drugs, 2d ed., pp. 59, 63, 64 (1999).
United States Pharmacopeia USP 23, NF 18 <941> "X-Ray Diffraction", pp. 1843-1844 (1995).
United States Pharmacopeia USP 28, NF 23 <941> "X-Ray Diffraction", pp. 2513-2515 (2005).
Brook, The Nomenclature of Relative Stereochemistry, J. of Chem. Ed., 64(3):218-220 (1987).
Maehr, A Proposed New Convention for Graphic Presentation of Molecular Geometry and Topography, J. of Chem. Ed., 62(2):114-120 (1985).
Moss, Basic Terminology of Stereochemistry (IUPAC Recommendations 1996), Pure & Appl. Chem., 68 (12):2193-2222 (1996).
Cross et al., Rules for the Nomenclature of Organic Chemistry—Section E: Stereochemistry (Recommendations 1974), Pure & Appl. Chem., 45(1-B):13-30 (1976).
Nasipuri, Stereochemistry of Organic Compounds, Principles and Applications, Chapter 4 (1994).
J. Brian Houston; Commentary, "Utility of In Vitro Drug Metabolism Data in Predicting In Vivo Metabolic Clearance; Biochemical Pharmacology", vol. 47, No. 9, pp. 1469-1479, 1994.
Martindale Thirty-third edition; "The Complete Drug Reference"; Pharmaceutical Press; pp. 1086-1089.

TRIAZOLO(4,5-D)PYRIMIDINE COMPOUNDS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This *is a reissue of U.S. Pat. No. 6,525,060, issued on Feb. 25, 2003, from U.S. patent application Ser. No. 09/508, 195, which* is a 371 National Phase application of PCT/SE99/02256, filed Dec. 2, 1999. *This reissue also claims the benefit of priority of Swedish Patent Application No. 9901271, filed Apr. 9, 1999, and Swedish Patent Application No. 9804211, filed Dec. 4, 1998.*

FIELD OF THE INVENTION

The present invention provides new triazolo[4,5-d]pyrimidine compounds, their use as medicaments, compositions containing them and processes for their preparation.

BACKGROUND OF THE INVENTION

Platelet adhesion and aggregation are initiating events in arterial thrombosis. Although the process of platelet adhesion to the sub-endothelial surface may have an important role to play in the repair of damaged vessel walls, the platelet aggregation that this initiates can precipitate acute thrombotic occlusion of vital vascular beds, leading to events with high morbidity such as myocardial infarction and unstable angina. The success of interventions used to prevent or alleviate these conditions, such as thrombolysis and angioplasty is also compromised by platelet mediated occlusion or re-occlusion.

A number of converging pathways lead to platelet aggregation. Whatever the initial stimulus, the final common event is a cross-linking of platelets by binding of fibrinogen to a membrane-binding site, glycoprotein IIb/IIIa (GPIIb/IIIa). The high anti-platelet efficacy of antibodies or antagonists for GPIIb/IIIa is explained by their interference with this final common event. However, this efficacy may also explain the bleeding problems that have been observed with this class of agent. Thrombin can produce platelet aggregation largely independently of other pathways but substantial quantities of thrombin are unlikely to be present without prior activation of platelets by other mechanisms. Thrombin inhibitors such as hirudin are highly effective anti-thrombotic agents, but again may produce excessive bleeding because they function as both anti-platelet and anti-coagulant agents (The TIMI 9a Investigators (1994), Circulation 90, pp. 1624-1630; The Global Use of Strategies to Open Occluded Coronary Arteries (GUSTO) IIIa Investigators (1994) Circulation 90, pp. 1631-1637; Neuhaus K. L. et. al. (1994) Circulation 90, pp. 1638-1642).

It has been found that adenosine 5'-diphosphate (ADP) acts as a key mediator of thrombosis. A pivotal role for ADP is supported by the fact that other agents, such as adrenaline and 5-hydroxytryptamine (5HT, serotonin) will only produce aggregation in the presence of ADP. The limited anti-thrombotic efficacy of aspirin may reflect the fact that it blocks only one source of ADP which is that released in a thromboxane-dependent manner following platelet adhesion (see e.g. Antiplatelet Trialists' Collaboration (1994), Br. Med. J. 308, pp. 81-106 and Antiplatelet Trialists' Collaboration (1994), Br. Med. J. 308, pp. 159-168). Aspirin has no effect on aggregation produced by other sources of ADP, such as damaged cells or ADP released under conditions of turbulent blood flow.

ADP-induced platelet aggregation is mediated by the $P_{2T}$ receptor subtype located on the platelet membrane. The $P_{2T}$ receptor (also known as $P2Y_{ADP}$ or $P2T_{AC}$) is primarily involved in mediating platelet aggregation/activation and is a G-protein coupled receptor which is as yet uncloned. The pharmacological characteristics of this receptor have been described, for example, in the references by Humphries et al., Br. J. Pharmacology (1994), 113, 1057-1063, and Fagura et al., Br. J. Pharmacology (1998) 124, 157-164. Recently it has been shown that antagonists at this receptor offer significant improvements over other anti-thrombotic agents (see J. Med. Chem. (1999) 42, 213). Accordingly there is a need to find further $P_{2T}$ ($P2Y_{ADP}$ or $P2T_{AC}$) antagonists as anti-thrombotic agents.

International Patent Application WO 9905143 discloses generically a series of triazolo[4,5-d]pyrimidine compounds having activity as $P_{2T}$ ($P2Y_{ADP}$ or $P2T_{AC}$) antagonists. It has now been found that certain compounds within the scope of International Patent Application WO 9905143 but not specifically disclosed therein exhibit high potency combined with surprisingly high metabolic stability and bioavailibility, such that the predicted therapeutic dose for prolonged inhibition of aggregation in man shows advantage.

DESCRIPTION OF THE INVENTION

In a first aspect the invention therefore provides a compound of formula (I):

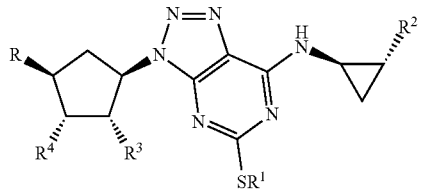

(I)

wherein:

$R^1$ is $C_{3-5}$ alkyl optionally substituted by one or more halogen atoms;

$R^2$ is a phenyl group, optionally substituted by one or more fluorine atoms;

$R^3$ and $R^4$ are both hydroxy;

R is XOH, where X is $CH_2$, $OCH_2CH_2$ or a bond;

or a pharmaceutically acceptable salt or solvate thereof, or a solvate of such a salt.

provided that:

when X is $CH_2$ or a bond, $R^1$ is not propyl.

when X is $CH_2$ and $R^1$ is $CH_2CH_2CF_3$, butyl or pentyl, the phenyl group at $R^2$ must be substituted by fluorine.

when X is $OCH_2CH_2$ and $R^1$ is propyl, the phenyl group at $R^2$ must be substituted by fluorine.

Alkyl groups, whether alone or as part of another group are straight chained and fully saturated.

Suitably $R^1$ is a $C_{3-5}$ alkyl optionally substituted by one or more fluorine atoms. Preferably $R^1$ is $C_{3-5}$ alkyl optionally substituted on the terminal carbon by three fluorine atoms. More preferably $R^1$ is 3,3,3,-trifluoropropyl, butyl or propyl.

Suitably $R^2$ is phenyl or phenyl substituted by one or more fluorine atoms. Preferably $R^2$ is phenyl, 4-fluorophenyl or 3,4-difluorophenyl.

Suitably R is XOH where X is $CH_2$, $OCH_2CH_2$ or a bond. Preferably R is $CH_2OH$ or $OCH_2CH_2OH$.

Particularly preferred compounds include:

[1R-[1α,2α,3β(1R*,2S*),5β]]-3-[7-[[2-(4-Fluorophenyl) cyclopropyl]amino]-5-[(3,3,3-trifluoropropyl)thio]-3H-1, 2,3-triazolo[4,5-d]pyrimidin-3-yl]-5-(hydroxymethyl)-cyclopentane-1,2-diol;

[1R-[1α,2α,3β(1R*,2S*),5β]]-3-[7-[[2-(3,4-Difluorophenyl)cyclopropyl]amino]-5-[(3,3,3-trifluoropropyl)thio]-3H-1,2,3-triazolo[4,5-d]pyrimidin-3-yl]-5-(hydroxymethyl)-cyclopentane-1,2-diol;

[1S-(1α,2α,3β(1S*,2R*),5β]]-3-[7-[[2-(3,4-Difluorophenyl)cyclopropyl]amino]-5-(propylthio)-3H-1,2,3-triazolo [4,5-d]pyrimidin-3-yl]-5-(2-hydroxyethoxy)-cyclopentane-1,2-diol;

[1R-[1α,2α,3β(1R*,2S*),5β]]-3-[5-(Butylthio)-7-[[2-(3,4-difluorophenyl)cyclopropyl]amino]-3H-1,2,3-triazolo[4, 5-d]pyrimidin-3-yl]-5-(hydroxymethyl)-cyclopentane-1, 2-diol;

[1S-[1α,2β,3β,4α(1S*,2R*)]]-4-[5-(Butylthio)-7-[[2-(4-fluorophenyl)cyclopropyl]amino]-3H-1,2,3-triazolo[4,5-d]pyrimidin-3-yl]-cyclopentane-1,2,3-triol;

[1S-(1α,2α,3β(1S*,2R*),5β)]-3-[7-[[2-(3,4-Difluorophenyl)cyclopropyl]amino]-5-[(3,3,3-trifluoropropyl)thio]-3H-1,2,3-triazolo[4,5-d]pyrimidin-3-yl]-5-(2-hydroxyethoxy)-cyclopentane-1,2-diol;

[1S-[1α,2α,3β,5β(1S*,2R*)]]-3-(2-Hydroxyethoxy)-5-[7-(2-phenylcyclopropyl)amino]-5-[(3,3,3-trifluoropropyl) thio]-3H-1,2,3-triazolo[4,5-d]pyrimidin-3-yl]-cyclopentane-1,2-diol [1S-[1α,2β,3β,4α(1S*, 2R*)]]-4-[5-(Butylthio)-7-[[2-(3,4-difluorophenyl)cyclopropyl] amino]-3H-1,2,3-triazolo[4,5-d]pyrimidin-3-yl] cyclopentane-1,2,3-triol;

[1S-[1α,2α,3β(1S*,2R*),5β]]-3-[5-(Butylthio)-7-[(2-phenylcyclopropyl)amino]-3H-1,2,3-triazolo[4,5-d]pyrimidin-3-yl]-5-(2-hydroxethoxy)-cyclopentane-1,2-diol;

and pharmaceutically acceptable salts or solvates thereof, or solvates of such salts.

According to the invention there is further provided a process for the preparation of a compound of formula (I) which comprises:

(a) reacting a compound of formula (II):

(II)

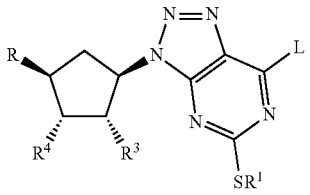

where R, $R^1$, $R^3$ and $R^4$ are as defined in formula (I), or are protected derivatives thereof, or $R^3$ and $R^4$ together form a bond in the 5-membered ring, or R is $CH_2CH_2OR'$, where R is $C_{1-6}$ alkyl or benzyl, and L is a leaving group such as halogen or SR, with a compound of formula (III):

(III)

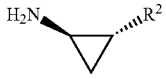

where $R^2$ is as defined in formula (I), or is a protected derivative thereof, or where X is a bond:

(b) hydroxylation of a compound of formula (IV):

(IV)

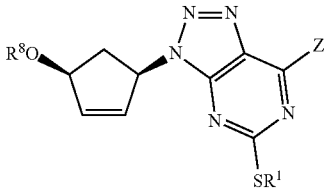

where $R^1$ is defined in formula (I) and $R^8$ is H or $CH_2CH_2OP^3$ where $P^3$ is H or a protecting group or $R^8$ is $CH_2COOR'$ where R' is $C_{1-6}$ alkyl or benzyl, and Z is $NH_2$ or

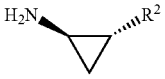

where $R^2$ is defined in formula (I).

and for both (a) and (b) optionally thereafter and in any order:

converting one or more functional groups into further functional groups;

removing any protecting groups;

forming a pharmaceutically acceptable salt or solvate, or a solvate of such a salt.

Compounds of formula (II) can be reacted with amines of formula (III) in the presence of a base, such as a tertiary organic amine, in an inert solvent, such as dichloromethane, at ambient or elevated temperature. Other suitable bases include inorganic bases such as potassium carbonate.

The hydroxy groups $R^3$ and $R^4$ can be protected as groups $OP^1$ and $OP^2$ where $P^1$ and $P^2$ are protecting groups. Examples of suitable protecting groups in compounds of formula (II) are $C_{1-6}$ alkyl (preferably methyl), benzyl, $(C_{1-6}alkyl)_3Si$ (preferably t-butyldimethylsilyl), and a C(O) $C_{1-6}$alkyl group such as acetyl. Preferably the two groups $P^1$ and $P^2$ together with the atoms to which they are attached form an alkylidene ring such as a methylidene or isopropylidene ring. Alternatively $P^1$ and $P^2$ can form an alkoxymethylidene ring such as ethoxymethylidene.

Protecting groups can be added and removed using known reaction conditions. The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

Ester protecting groups can be removed by basic hydrolysis, for example by using a metal hydroxide, preferably an alkali metal hydroxide, such as sodium hydroxide or lithium hydroxide, or quaternary ammonium hydroxide in a solvent, such as aqueous ethanol or aqueous tetrahydrofuran, at a temperature of from 10° to 100° C., preferably the temperature is around room temperature; or by acidic hydrolysis using a mineral acid such as HCl or a strong organic acid such as trichloroacetic acid in a solvent such as aqueous 1,4-dioxane. Trialkylsilyl protecting groups can be removed by the use of, for example, a fluoride ion source, for example tetra-n-butylammonium fluoride or hydrogen fluoride. When one or both of $P^1$ and are $C_{1-6}$ alkyl, deprotection can be achieved using boron tribromide. Benzyl groups can be removed by hydrogenolysis using a transition metal catalyst, for example palladium on charcoal, under an atmosphere of hydrogen, at a pressure of from 1 to 5 bar, in a solvent, such as acetic acid.

A compound of formula (II) can be prepared by diazotising a compound of formula (V):

(V)

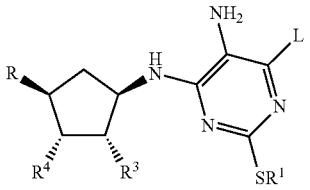

wherein $R^1$ is as defined in formula (I), and R is as defined in formula (I), or is a protected derivative thereof, or is $OCH_2CO_2R'$, where R' is $C_{1-6}$ alkyl or benzyl, and L is as defined above and $R^3$ and $R^4$ are as defined in formula (I) or are protected derivatives thereof or $R^3$ and $R^4$ together form a bond in the 5-membered ring, with a metal nitrite, for example an alkali metal nitrite, especially sodium nitrite in dilute aqueous acid, for example 2M HCl, or with a $C_{1-6}$-alkyl nitrite, in an inert solvent, at a temperature of from about −20 to about 100° C. Preferred conditions are isoamyl nitrite in acetonitrile at about 80° C.

A compound of formula (V) wherein R is $CH_2OH$, $R^3$ and $R^4$ are hydroxyl or protected derivatives thereof and L is as defined above, can be prepared by reducing a compound of formula (VI):

(VI)

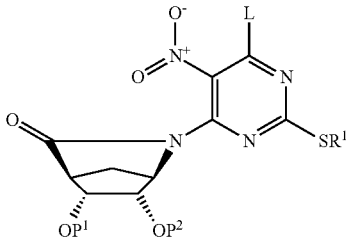

wherein $R^1$, L, $P^1$ and $P^2$ are as defined above.

The reduction of the nitro group can be carried out for example by using hydrogenation with a transition metal catalyst at a temperature around room temperature, for example palladium on charcoal under an atmosphere of hydrogen, preferably at a pressure from 1 to 5 atmospheres, in a solvent, for example ethanol, or by using iron in an acidic solvent such as acetic acid at a temperature of about 100° C.

Reduction of the lactam can be carried out using complex metal hydrides such as lithium aluminium hydride in a solvent such as ether or preferably, by using sodium borohydride in a suitable solvent such as methanol.

A compound of formula (VI) can be prepared by reacting a compound of formula (VII):

(VII)

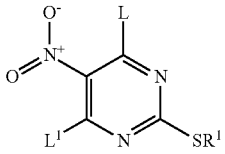

wherein L and $R^1$ are as defined above and $L^1$ is a leaving group, for example a halogen atom, wherein L and $L^1$ are preferably the same, with a compound of formula (VIII):

(VIII)

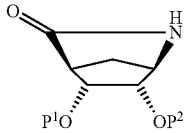

wherein $P^1$ and $P^2$ are as defined above, in the presence of a base such as $C_{1-6}$-alkyl-M or MH wherein M is a metal ion, for example n-butyl lithium, in an inert solvent, such as tetrahydrofuran, at a temperature of from about −10 to about 100° C. Preferably sodium hydride is used in tetrahydrofuran at room temperature.

One or more functional groups can be converted into further functional groups using standard chemistry. A compound where X is a bond can be converted to a compound where X is $O(CH_2)_2$ by treatment with base followed by LY where L is a leaving group and Y is $(CH_2)_2OH$ or a protected version thereof or Y is $CH_2COOR'$ where R' is $C_{1-6}$ alkyl or benzyl. A compound where R is $CH_2CH_2OR$ may be converted into a compound where R is $O(CH_2)_2OH$ by reduction, for example using DIBAL-H®. The group $SR^1$ can be interconverted by oxidation of the sulfur, for example using oxone™ or mCBPA, followed by treatment with a compound $R^{1'}$-SM where $R^{1'}$ is a different $R^1$ group and M is a metal such as sodium. Alternatively the product of the sulfur oxidation may be treated with MSH where M is a metal such as sodium, followed by treatment with a base and $R^{1'}X$ where $R^{1'}$ is a different $R^1$ group and X is a leaving group. Suitable bases include N,N-diisopropylethylamine.

A compound of formula (II) where R, $R^1$, $R^3$, and $R^4$ are as defined in formula (I) or are protected derivatives thereof, or $R^3$ and $R^4$ together form a bond in the 5-membered ring, or R is $OCH_2CO_2R'$ where R' is $C_{1-6}$ alkyl or benzyl, and L is a leaving group such as halogen, may be converted into a compound of formula (II) where R, $R^1$, $R^3$, and $R^4$ are defined above and L is $NH_2$ by treatment with a diazotizing agent in the presence of a halogenating agent, preferably isoamyl-nitrite and carbon tetrabromide.

A compound of formula (II) where R, $R^1$, $R^3$, and $R^4$ are defined above and L is $NH_2$ may be prepared by treating a compound of formula (II) where R, $R^1$, $R^3$, and $R^4$ are as defined above and L is a leaving group such as halogen, with ammonia in a solvent such as methanol.

Compounds of formula (V) can also be prepared by treating a compound of formula (XI)

(XI)

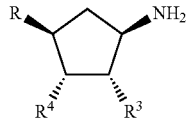

where R, $R^3$ and $R^4$ are as defined in formula (I) or are protected derivatives thereof or R is $OCH_2CO_2R'$ where R' is $C_{1-6}$ alkyl or benzyl, or $R^3$ and $R^4$ together form a bond in the 5-membered ring, with a compound of formula (VII) as defined above, followed by reduction of the nitro group. The reaction is carried out in an inert solvent such as dichloromethane or 1,4-dioxane, in the presence of a non-nucleophilic base, such as N,N-diisopropylamine, at a tempeature of about −20° C. to about 150° C., preferably at ambient temperature.

Compounds of formula (II) where R is as defined in formula (I), $R^3$ and $R^4$ together form a bond in the 5-membered ring, and L is $SR^1$, or a protected derivative thereof, can be prepared by reacting a compound of formula (XII):

(XII)

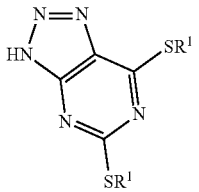

where $R^1$ groups are as defined in formula (I), with a compound of formula (XIII):

(XIII)

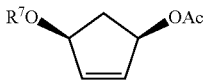

in which $R^7$ is H or a protected derivative thereof. The reaction can be carried out in the presence of a suitable transition metal complex, preferably tetrakistriphenylphosphine palladium(0).

Compounds of formula (XII) can be prepared from compounds of formula (XIV):

(XIV)

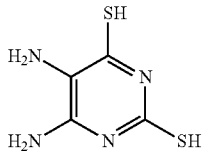

by reacting with a compound $R^1X$ where $R^1$ is as defined in formula (I) and X is a leaving group such as halo, followed by cyclisation.

Compounds of formula (XI) where R is OH or a protected version thereof and $R^3$ and $R^4$ are as defined in formula (I) or are protected derivatives thereof may be prepared from compounds of formula (XIII) where $R^7$ is H or a protecting group by treatment with a bisester of imidodicarbamic acid using palladium catalysis followed by hydroxylation of the double bond, and optionally, deprotection of the nitrogen. Preferably imidodicarbonic acid, bis-(1,1-dimethylethyl) ester and tetrakistriphenylphosphine palladium(0) are used followed by osmium tetroxide and deprotection using hydrochloric acid in methanol.

Compounds of formula (XI), where R is $OCH_2CO_2R'$ where R' is $C_{1-6}$ alkyl and $R^3$ and $R^4$ together form a bond in the 5-membered ring, may be formed from compounds of formula (XIII), where $R^7$ is H or a protecting group, by treatment with an azide in the presence of a palladium catalyst, followed by reduction of the azide and alkylation of the alcohol as described previously.

Compounds of formula (XI) where R is $OCH_2CH_2OH$ and $R^3$ and $R^4$ are as defined in formula (I) or are protected derivatives thereof may be prepared from compounds of formula (XI) where R is OH and $R^3$ and $R^4$ are as defined in formula (I) or are protected derivatives thereof, by protection of the nitrogen, alkylation of the alcohol using a 2-halo-acetic acid ester, followed by reduction of the ester and deprotection of the nitrogen. We prefer protection of the nitrogen as a carbobenzyloxy derivative using benzyl chloroformate followed by alkylation of the alcohol using ethyl bromoacetate and potassium t-butoxide, reduction of the ester using lithium borohydride in tetrahydrofuran and deprotection of the nitrogen by hydrogenation in the presence of palladium on carbon. In addition we prefer the case where the alcohols $R^3$ and $R^4$ are protected as an isopropylidene ring.

The amines of formula (III) can be prepared using procedures described in H Nishiyama et al, Bull. Chem. Soc., Jpn., 1995, 68, 1247, P. Newman, Optical Resolution Procedures for Chemical Compounds, Vol. 1, Amines and Related Compounds; Optical Resolution and Information Centre: Manhattan College, Riverdale, N.Y., 1978, p120, J. Vallgarda et al, J. Chem. Soc. Perkin 1, 1994, 461 or in International Patent Application WO 9905143.

All novel intermediates form a further aspect of the invention.

Salts of the compounds of formula (I) may be formed by reacting the free acid, or a salt thereof, or the free base, or a salt or a derivative thereof, with one or more equivalents of the appropriate base (for example ammonium hydroxide optionally substituted by $C_{1-6}$-alkyl or an alkali metal or alkaline earth metal hydroxide) or acid (for example a hydrohalic (especially HCl), sulphuric, oxalic or phosphoric acid). The reaction may be carried out in a solvent or medium in which the salt is insoluble or in a solvent in which the salt is soluble, e.g. water, ethanol, tetrahydrofuran or diethyl ether, which may be removed in vacuo, or by freeze drying. The reaction may also be a metathetical process or it may be carried out on an ion exchange resin. The non-toxic physiologically acceptable salts are preferred, although other salts may be useful, e.g. in isolating or purifying the product.

The compounds of the invention act as $P_{2T}$ ($P2Y_{ADP}$ or $P2T_{AC}$) receptor antagonists. Accordingly, the compounds are useful in therapy, including combination therapy, particularly they are indicated for use as: inhibitors of platelet activation, aggregation and degranulation, promoters of platelet disaggregation, anti-thrombotic agents or in the treatment or prophylaxis of unstable angina, primary arterial thrombotic complications of atherosclerosis such as thrombotic or embolic stroke, transient ischaemic attacks, peripheral vascular disease, myocardial infarction with or without thrombolysis, arterial complications due to interventions in atherosclerotic disease such as angioplasty, including coronary angioplasty (PTCA), endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopaenic purpura, haemolytic uraemic syndrome, thrombotic complications of septicaemia, adult respiratory distress syndrome, anti-phospholipid syndrome, heparin-induced thrombocytopaenia and pre-eclampsia/eclampsia, or venous thrombosis such as deep vein thrombosis, venoocclusive disease, haematological conditions such as myeloproliferative disease, including thrombocythaemia, sickle cell disease; or in the prevention of mechanically-induced platelet activation in vivo, such as cardiopulmonary bypass and extracorporeal membrane oxygenation (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine, Raynaud's phenomenon, conditions in which platelets can contribute to the underlying inflammatory disease process in the vascular wall such as atheromatous plaque formation/progression, stenosis/restenosis and in other inflammatory conditions such as asthma, in which platelets and platelet-derived factors are implicated in the immunological disease process. Further indications include treatment of CNS disorders and prevention of the growth and spread of tumours.

According to the invention there is further provided the use of a compound according to the invention as an active ingredient in the manufacture of a medicament for use in the treatment or prevention of the above disorders. In particular the compounds of the invention are useful for treating myocardial infarction, thrombotic stroke, transient ischaemic attacks, peripheral vascular disease and stable and unstable angina, especially unstable angina. The invention also provides a method of treatment or prevention of the above disorders which comprises administering to a person suffering from or susceptible to such a disorder a therapeutically effective amount of a compound according to the invention.

The compounds may be administered topically, e.g. to the lung and/or the airways, in the form of solutions, suspensions, HFA aerosols and dry powder formulations; or systemically, e.g. by oral administration in the form of tablets, pills, capsules, syrups, powders or granules, or by parenteral administration in the form of sterile parenteral solutions or suspensions, by subcutaneous administration, or by rectal administration in the form of suppositories or transdermally.

The compounds of the invention may be administered on their own or as a pharmaceutical composition comprising the compound of the invention in combination with a pharmaceutically acceptable diluent, adjuvant and/or carrier. Particularly preferred are compositions not containing material capable of causing an adverse, e.g. an allergic, reaction.

Dry powder formulations and pressurised HFA aerosols of the compounds of the invention may be administered by oral or nasal inhalation. For inhalation the compound is desirably finely divided. The compounds of the invention may also be administered by means of a dry powder inhaler. The inhaler may be a single or a multi dose inhaler, and may be a breath actuated dry powder inhaler.

One possibility is to mix the finely divided compound with a carrier substance, e.g. a mono-, di- or polysaccharide, a sugar alcohol or another polyol. Suitable carriers include sugars and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, e.g. that known as the Turbuhaler® in which a dosing unit meters the desired dose which is then inhaled by the patient. With this system the active compound with or without a carrier substance is delivered to the patient.

The pharmaceutical composition comprising the compound of the invention may conveniently be tablets, pills, capsules, syrups, powders or granules for oral administration; sterile parenteral or subcutaneous solutions, suspensions for parenteral administration or suppositories for rectal administration.

For oral administration the active compound may be admixed with an adjuvant or a carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet may be coated with a suitable polymer dissolved either in a readily volatile organic solvent or an aqueous solvent.

For the preparation of soft gelatine capsules, the compound may be admixed with e.g. a vegetable oil or polyethylene glycol. Hard gelatine capsules may contain granules of the compound using either the above mentioned excipients for tablets, e.g. lactose, saccharose, sorbitol, mannitol, starches, cellulose derivatives or gelatine. Also liquid or semisolid formulations of the drug may be filled into hard gelatine capsules.

Liquid preparations for oral application may be in the form of syrups or suspensions, for example solutions containing the compound, the balance being sugar and a mixture of ethanol, water, glycerol and propylene glycol. Optionally such liquid preparations may contain colouring agents, flavouring agents, saccharine and carboxymethylcellulose as a thickening agent or other excipients known to those skilled in art.

EXAMPLES

The invention is illustrated by the following non-limiting examples.

In the examples the NMR spectra were measured on a Varian Unity Inova 300 or 400 spectrometer and the MS spectra were measured as follows: EI spectra were obtained on a VG 70-250S or Finnigan Mat Incos-XL spectrometer, FAB spectra were obtained on a VG70-250SEQ spectrometer, ESI and APCI spectra were obtained on Finnigan Mat SSQ7000 or a Micromass Platform spectrometer. Preparative HPLC separations were generally performed using a Novapak®, Bondapak® or Hypersil® column packed with BDSC-18 reverse phase silica. Flash chromatography (indicated in the Examples as ($SiO_2$)) was carried out using Fisher Matrix silica, 35-70 μm. For examples which showed the presence of rotamers in the proton NMR spectra only the chemical shifts of the major rotamer are quoted.

Example 1

[1R-[1α,2α,3β(1R*,2S*),5β]]-3-[7-[[2-(4-Fluorophenyl)cyclopropyl]amino]-5-[(3,3,3-trifluoropropyl)thio]-3H-1,2,3-triazolo[4,5-d]pyrimidin-3-yl]-5-(hydroxymethyl)-cyclopentane-1,2-diol a) [3aS-[1(E),3aα,6α,7aβ]]-1-[3-(4-Fluorophenyl)-1-oxo-2-propenyl]-hexahydro-8,8-dimethyl-3H-3a,6-methano-2,1-benzisothiazole-2,2-dioxide A mixture of 3-(4-fluorophenyl)-2-propenoic acid (3.0 g) and thionyl chloride (5.0 ml) was stirred at 70° C. for 1 hour, the reaction mixture was then concentrated under reduced pressure. The residue was azeotroped twice with dichloromethane then dissolved in toluene (10 ml). To a suspension of sodium hydride (60% dispersion in oil; 0.99 g) in toluene (40 ml) was added a solution of [3aS-(3aα,6α,7aβ)]-hexahydro-8,8-dimethyl-3H-3a,6-methano-2,1-benzisothiazole-2,2-dioxide (3.89 g) in toluene (40 ml) and the mixture stirred for 30 minutes. To the reaction mixture was then added the solution described above and the resulting suspension was stirred for 16 hours. Water (200 ml) was added, the organics collected and the aqueous extracted into dichloromethane (3×100 ml). The organics were combined, dried and concentrated. Recrystallisation (ethanol) gave the subtitle compound as colourless needles (5.92 g).

MS (APCI) 364 ($M+H^+$,100%)

b) [3aS-[1(1S*,2S*),3aα,6α,7aβ]]-1-[[2-(4-Fluorophenyl)cyclopropyl]carbonyl]-hexahydro-8,8-dimethyl-3H-3a,6-methano-2,1-benzisothiazole-2,2-dioxide A solution of diazomethane (2.9 g) in ether (150 ml) (prepared as described in Vogel's Textbook of Practical Organic Chemistry, Fifth Edition, Longman Scientific and Technical, p432) was added to a solution of the product of step a) (5.90 g) and palladium(II) acetate (18 mg) in dichloromethane (350 ml) at 0° C. and the reaction mixture stirred at 0° C. for 5 hours. Acetic acid (5 ml) was added and the reaction mixture was then washed with saturated sodium bicarbonate solution (200 ml) and the organics filtered through a plug of silica. After concentrating in vacuo, the residue was recrystallised (ethanol) to give the subtitle compound as colourless needles (3.81 g).

MS (APCI) 378 ($M+H^+$,100%)

c) (1R-trans)-2-(4-Fluorophenyl)-cyclopropanecarboxylic acid

A suspension of the product from step b) (3.74 g) and lithium hydroxide monohydrate (4.11 g) in tetrahydrofuran (100 ml)/ water (3 ml) was stirred at 50° C. for 24 hours. The reaction mixture was concentrated in vacuo, and the residue dissolved in water (100 ml), acidified with 2N HCl and extracted into dichloromethane (3×75 ml). The organics were dried and concentrated. Purification ($SiO_2$, isohexane: diethylether 2:1 as eluant) gave the subtitle compound as a colourless solid (1.78 g).

MS (APCI) 179 ($M-H^+$,100%)

d) (1R-trans)-2-(4-Fluorophenyl)cyclopropanamine, [R-(R*,R*)]-2,3-dihydroxybutanedioate (1:1)

To a solution of the product from step c) (1.78 g) and triethylamine (2.7 ml) in acetone/water (10:1, 23 ml) at 0° C. was added ethyl chloroformate (2.0 ml) over 5 min. The solution was maintained at 0° C. for 30 minutes before addition of sodium azide (1.52 g) in water (6 ml). After a further hour, water (350 ml) was added and the reaction mixture extracted with toluene (3×100 ml). The organic extracts were combined and dried, then heated at reflux for 2 hours behind a blast screen. After cooling the solution, 6N HCl (50 ml) was added and the mixture heated at reflux for 3 hours. Water (150 ml) was added and the aqueous phase basified with 2N NaOH (aq), then extracted into dichloromethane (3×100 ml). The organic phase was dried and concentrated. The amine was dissolved in ethanol (5 ml) and a solution of L-tartaric acid (1.48 g) in ethanol (20 ml) was added. After 20 minutes the solid was collected affording the subtitle compound as colourless needles (1.12 g).

NMR δH ($d_6$-DMSO) 1.07-1.39 (1H, m), 1.22-1.29 (1H, m), 2.16-2.23 (1H, m), 2.64-2.70 (1H,m), 3.95 (2H, s), 7.06-7.19 (4H, m)

e) [3aR-[3aα,4α,6α(1R*,2S*),6aα]]-6-[7-[[2-(4-Fluorophenyl)cyclopropyl]amino]-5-(propylthio)-3H-1,2,3-triazolo[4,5-d]pyrimidin-3-yl]-tetrahydro-2,2-dimethyl-4H-cyclopenta-1,3-dioxole-4-methanol N,N-Diisopropylethylamine (1.29 g) was added to a solution of [3aR-(3aα,4α,6α,6aα)]-6-[7-chloro-5-(propylthio)-3H-1,2,3-triazolo[4,5-d]pyrimidin-3-yl]-tetrahydro-2,2-dimethyl-4H-cyclopenta-1,3-dioxole-4-methanol (prepared as described in International Patent Application WO 9703084) (1.0 g) and the product of step d) (0.75 g) in dichloromethane (25 ml). The reaction mixture was stirred at room temperature for 3 hours, then washed with water, dried and evaporated. The residue was purified ($SiO_2$, ethyl acetate: isohexane 1:1 as eluent) to afford the subtitle compound (1.25 g).

MS (APCI) 515 ($M+H^+$, 100%)

f) [3aR-[3aα,4α,6α(1R*,2S*),6aα]]-6-[7-[[2-(4-Fluorophenyl)cyclopropyl]amino]-5-(propylsulphonyl)-3H-1,2,3-triazolo[4,5-d]pyrimidin-3-yl]-tetrahydro-2,2-dimethyl-4H-cyclopenta-1,3-dioxole-4-methanol 3-Chloroperoxybenzoic acid (70%, 1.8 g) was added to a suspension of the product of step e) (1.25 g) in ethanol (25 ml) and the resulting solution stirred at room temperature for 2 hours. The reaction mixture was concentrated and the residue taken up in ethyl acetate (500 ml), washed with 10% aqueous sodium metabisulfite solution (2×100 ml) and 10% aqueous sodium bicarbonate solution (2×100 ml) then dried and concentrated to afford the subtitle compound (1.4 g).

MS (APCI) 547 ($M+H^+$, 100%)

g) [[3aR-[3aα,4α,6α(1R*,2S*),6aα]]-6-[7-[[2-(4-Fluorophenyl)cyclopropyl]amino]-5-[(3,3,3-trifluoropropy)lthio]-3H-1,2,3-triazolo[4,5d]pyrimidin-3-yl)-tetrahydro-2,2-dimethyl-4H-cyclopenta-1,3-dioxole-4-methanol Sodium hydrosulfide hydrate (1.4 g) was added to a solution of the product of step f) (1.4 g) in dimethyl sulphoxide (20 ml) and the solution stirred at room temperature for 1.5 hours. Brine (150 ml) was added and the mixture acidified with acetic acid then extracted with ethyl acetate (3×100 ml). The organic phase was dried and concentrated and the residue azeotroped with toluene (3×100 ml). The residue was dissolved in N,N-dimethylformamide (20 ml) then N,N-diisopropylethylamine (0.33 g) and 3,3,3-trifluoropropylbromide (0.48 g) added. After stirring at 50° C. for 30 minutes the reaction mixture was diluted with ethyl acetate (100 ml) then washed with aqueous brine (3×100 ml), dried and concentrated then the residue purified ($SiO_2$, isohexane:ethyl acetate 1:1 as eluant) to afford the subtitle compound (1.4 g).

MS (APCI) 569 ($M+H^+$, 100%)

h) [1R-[1α,2α,3β(1R*2S*),5β]]-3-[7-[[2-(4-Fluorophenyl)cyclopropyl]amino]-5-[(3,3,3-trifluoropropyl)thio]-3H-1,2,3-triazolo[4,5-d]pyrimidin-3-yl]-5-(hydroxymethyl)-cyclopentane-1,2-diol A solution of the product from step g) (1.4 g) in trifluoroacetic acid (10 ml) and water (2 ml) was stirred at room temperature for 1 hour. The reaction mixture was diluted with ethyl acetate (400 ml) then washed with sodium bicarbonate solution (400 ml), dried and evaporated. The residue was purified ($SiO_2$, methanol:chloroform 3:47 as eluant) to afford the title compound (0.44 g).

MS (APCI) 529 ($M+H^+$,100%)

NMR δH ($d_6$-DMSO) 9.42 (1H, d), 7.27-7.22 (2H, m), 7.14-7.08 (2H, m), 5.01-4.95 (2H, m), 4.73-4.70 (2H, m), 4.44-4.41 (1H, m), 3.87-3.84 (1H, m), 3.50-3.45 (2H, m), (3H, m), 2.60-2.55 (1H, m), 2.28-2.20 (2H, m), 2.10-2.06 (1H, m), 1.90-1.8 (1H, m), 1.49-1.46 (1H, m), 1.33-1.30 (1H, m).

Example 2

[1R-[1α,2α,3β(1R*,2S*),5β]]-3-[7-[[2-(3,4-Difluorophenyl)cyclopropyl]amino]-5-[(3,3,3-trifluoropropyl)thio]-3H-1,2,3-triazolo[4,5-d]pyrimidin-3-yl]-5-(hydroxymethyl)-cyclopentane-1,2-diol a) [3aS-[1(E),3aα,6α,7aβ]]-1-[3-(3,4-Difluorophenyl)-1-oxo-2-propenyl]-hexahydro-8,8-dimethyl-3H-3a,6-methano-2,1-benzisothiazole-2,2-dioxide The subtitle compound was prepared according to the method of Example 1, step a) using 3-(3,4-difluorophenyl)-2-propenoic acid.

MS (APCI) 382 ($M+H^+$, 100%)

b) [3aS-[1(1S*,2S*),3aα,6α,7aβ]]-1-[[2-(3,4-Difluorophenyl)cyclopropyl]carbonyl]-hexahydro-8,8-dimethyl-3H-3a,6-methano-2,1-benzisothiazole-2,2-dioxide The subtitle compound was prepared according to the method of Example 1, step b) using the product of step a).

MS (APCI) 396 ($M+H^+$, 100%)

c)(1R-trans)-2-(3,4-Difluorophenyl)-cyclopropane carboxylic acid

The subtitle compound was prepared according to the method of Example 1, step c) using the product of step b).

NMR δH ($CDCl_3$) 7.06 (1H, dt, J=10.0, J=8.5 Hz), 6.93-6.80 (2H, m), 2.58-2.52 (1H, m), 1.88-1.82 (1H, m), 1.66 (1H,dt, J=9.2, J=5.2 Hz), 1.34 (1H, ddd, J=8.5, J=6.5, J=4.8 Hz).

d)(1R-trans)-2-(3,4-Difluorophenyl)cyclopropanamine, [R-(R*,R*)]-2,3-dihydroxybutanedioate (1:1)

The subtitle compound was prepared according to the method of Example 1, step d) using the product of step c).

MS (APCI) 170 ($M+H^+$, 100%)

e)[3aR-[3aα,4α,6α(1R*,2S*),6aα]-6-[7-[[2-(3,4-Difluorophenyl)cyclopropyl]amino]-5-[(3,3,3-trifluoropropyl) thio]-3H-1,2,3-triazolo[4,5-d]pyrimidin-3-yl]-tetrahydro-2,2-dimethyl-4H-cyclopenta-1,3-dioxole-4-methanol Isoamyl nitrite (5.1 ml) was added to a solution of [3aR-(3aα,4α,6α,6aα)]-6-[[5-amino-6-Chloro-2-[(3,3,3-trifluoropropyl)thio]-4-pyrimidinyl]-amino]-tetrahydro-2,2-dimethyl-4H-cyclopenta-1,3-dioxole-4-methanol (prepared as described in International Patent Application WO 9703084) (8.1 g) in acetonitrile (1000 ml) and the solution heated at 70° C. for 1 hour. The cooled reaction mixture was concentrated and purified ($SiO_2$, dichloromethane:ethyl acetate 4:1 as eluant) to afford an intermediate which was converted to the subtitle compound by the method of example 1, step e) using the product of step d).

MS (APCI) 587 ($M+H^+$, 100%)

f) [1R-[1α,2α,3β(1R*,2S*),5β]]-3-[7-[[2-(3,4-Difluorophenyl)cyclopropyl]amino]-5-[(3,3,3-trifluoropropyl)thio]-3H-1,2,3-triazolo[4,5-d]pyrimidin-3-yl]-5-(hydroxymethyl)-cyclopentane-1,2-diol Prepared according to the method of example 1, step h) using the product of step e).

MS (APCI) 547 ($M+H^+$, 100%)

NMR δH ($d_6$-DMSO) 9.43 (1H, d), 7.35-7.28 (2H, m), 7.14-7.02 (1H, m), 5.01-4.96 (2H, m), 4.72-4.69 (2H, m), 4.42 (1H, q), 3.87-3.84 (1H, m), 3.50-3.44 (2H, m), 3.25-3.12 (3H, m), 2.58-2.50 (2H, m), 2.28-2.21 (3H, m), 1.85-1.80 (1H, m), 1.52-1.50 (1H, m), 1.39-1.37 (1H, m).

Example 3

[1S-(1α,2α,3β(1S*,2R*),5β)]-3-[7-[2-(3,4-Difluorophenyl)cyclopropyl]amino]-5-(propylthio)-3H-1,2,3-triazolo[4,5-d]pyrimidin-3-yl)-5-(2-hydroxyethoxy)-cyclopentane-1,2-diol, a) (1R-cis)-Bis(1,1-dimethylethyl)-4-hydroxy-2-cyclopentenylimidodicarbonate To a suspension of ether washed sodium hydride (60% dispersion in oil; 0.31 g) in tetrahydrofuran (30 ml) was added imidodicarbonic acid bis-(1,1-dimethylethyl)ester (1.84 g). The mixture was stirred at 40° C. for 1 hour. To the mixture, at ambient temperature, was then added (1S-cis)-4-acetoxy-2-cyclopenten-1-ol (0.5 g) and tetrakis (triphenylphosphine)palladium(0) (0.18 g). The reaction mixture was stirred for 24 hours then purified ($SiO_2$, ethyl acetate: hexane 1:9 as eluant) to give the subtitle compound as a colourless solid (0.90 g).

NMR δH ($d_6$-DMSO) 1.43 (18H, s), 1.61 (1H, ddd, J=12.3, 7.7, 6.4 Hz), 2.54 (1H, dt, J=12.6, 7.4 Hz), 4.51-4.57 (1H, m), 4.86 (1H, tq, J=8.0, 1.8 Hz), 4.91 (1H, d, J=5.4 Hz), 5.71-5.77 (2H, m).

b) [1R-(1α,2β,3β,4α)]-2,3,4-Trihydroxycyclopentenylimidodicarbonic acid, bis(1,1-dimethylethyl) ester To a solution of the product of step a) (17.1 g) in tetrahydrofuran (500 ml)/water (50 ml) was added N-methylmorpholine-N-oxide (9.4 g) followed by osmium tetroxide (10 ml, 2.5% solution in t-butanol). The mixture was stirred at room temperature for 4 days then treated with sodium hydrosulphite (6.0 g). The suspension was filtered through celite and the product purified ($SiO_2$, ethyl acetate:hexane 1:1 as eluant) to afford the subtitle compound (19.1 g).

NMR δH ($d_6$-DMSO) 1.44 (18H, s), 1.46-1.60 (1H, m), 1.97-2.05 (1H, m), 3.55-3.58 (1H, m), 3.66-3.73 (1H, m), 4.11-4.21 (2H, m), 4.54 (1H, d, J=4.8 Hz), 4.56 (1H, d, J=5.9 Hz), 4.82 (1H, d, J=4.6 Hz)

c) [3aR-(3aα,4α,6α,6aα)]-6-Amino-tetrahydro-2,2-dimethyl-4H-cyclopenta-1,3-dioxol-4-ol, hydrochloride The product from step b) (17.4 g) in 6M HCl (100 ml)/methanol (500 ml) was stirred for 18 hours. The mixture was evaporated and then azeotroped with toluene (4×200 ml) to give a colourless powder (8.7 g). This solid was suspended in acetone (250 ml) containing 2,2-dimethoxypropane (25 ml) and cHCl (0.2 ml) then heated under reflux for 2 hours. The mixture was cooled, evaporated and azeotroped with toluene (3×200 ml). The residue was dissolved in 20% aqueous acetic acid and stirred for 2 hours. The mixture was evaporated and azeotroped with toluene (4×200 ml) to afford the subtitle compound (10.1 g).

MS (APCI) 174 ($M+H^+$, 100%)

d) [3aR-(3aα,4α,6α,6aα)]-6-[[6-Chloro5-nitro2-(propylthio)-pyrimidin-4yl]amino]-tetrahydro-2,2-dimethyl-4H-cyclopenta-1,3-dioxol-4-ol A solution of the product from step c) (10.0 g) and N,N-diisopropylethylamine (35 ml) in tetrahydrofuran (600 ml) was stirred for 1 hour. The mixture was filtered and the solution was added over 1 hour to a solution of 4,6-dichloro-5-nitro-2-(propylthio)-pyrimidine (prepared as described in International Patent Application WO 9703084) (25.6 g) in tetrahydrofuran (1000 ml) and stirred for a further 2 hours. The solvent volume was reduced in vacuo and ethyl acetate was added (1000 ml). The mixture was washed with water and the organic layers were dried. evaporated and purified ($SiO_2$, isohexane-ethyl acetate as eluant) to afford the subtitle compound (14.2 g).

MS (APCI) 405 ($M+H^+$, 100%)

e) [3aR-(3aα,4α,6α,6aα)]-6-[[5-Amino-6-Chloro-2-(propylthio)-pyrimidin-4-yl]amino]-tetrahydro-2,2-dimethyl-4H-cyclopenta-1,3-dioxol-4-ol Iron powder (3.0 g) was added to a stirred solution of the product of step d) (2.7 g) in acetic acid (100 ml). The reaction mixture was stirred at room temperature for 2 hours, concentrated to half volume, diluted with ethyl acetate and washed with water. The organic phase was dried and concentrated to afford the subtitle compound (2.0 g).

MS (APCI) 375 ($M+H^+$, 100%)

f) [3aR-(3aα,4α,6α,6aα)]-6-[7-Chloro-5-(propylthio)-3H-1,2,3-triazolo[4,5-d]-pyrimidin-3-yl]-tetrahydro-2,2-dimethyl-4H-cyclopenta-1,3-dioxol-4-ol Isoamyl nitrite (1.1 ml) was added to a solution of the product of step e) (2.0 g) in acetonitrile (100 ml) and the solution heated at 70° C. for 1 hour. The cooled reaction mixture was concentrated and purified ($SiO_2$, ethyl acetate: isohexane 1:3 as eluant) to afford the subtitle compound (1.9 g).

MS (APCI) 386 ($M+H^+$, 100%)

g) [3aR-(3aα,4α,6α,6aα)]-6-[7-Amino-5-(propylthio)-3H-1,2,3-triazolo[4,5-d]-pyrimidin-3-yl]-tetrahydro-2,2-dimethyl-4H-cyclopenta-1,3-dioxol-4-ol The product of step f) (13.2 g) in tetrahydrofuran (200 ml) containing 0.88 ammonia (5 ml) was stirred for 2 hours then concentrated to dryness and the residue partitioned between water and ethyl acetate. The organics were dried and then concentrated to afford the subtitle compound (12.5 g).

MS (APCI) 367 ($M+H^+$, 100%).

h) [3aR-(3aα,4α,6α,6aα)]-[[6-[7-Amino-5-(propylthio)-3H-1,2,3-triazolo[4,5-d]-pyrimidin-3-yl]-tetrahydro-2,2-dimethyl-4H-cyclopenta-1,3-dioxol-4-ol]oxy]acetic acid, methyl ester To a solution of the product of step g) (0.50 g) in tetrahydrofuran (25 ml) at 0° C., was added butyllithium (0.62 ml of 2.5N in hexanes). After 20 minutes, the suspension was treated with a solution of trifluoromethanesulfonyloxy-acetic acid methyl ester (0.34 g) (prepared according to the method of Biton, Tetrahedron, 1995, 51, 10513) in tetrahydrofuran (10 ml). The resulting solution was allowed to warm to room temperature then concentrated and purified ($SiO_2$, ethyl acetate: hexane 4:6 as eluant) to afford the subtitle compound (0.25 g).

MS (APCI) 439 ($M+H^+$, 100%).

i) [3aR-(3aα,4α,6α,6aα)]-[[6-[7-Bromo-5-(propylthio)-3H-1,2,3-triazolo[4,5-d]-pyrimidin-3-yl]-tetrahydro-2,2-dimethyl-4H-cyclopenta-1,3-dioxol-4-ol]oxy]acetic acid, methyl ester The product from step h) (1.1 g) and isoamylnitrite (2.4 ml) in bromoform (30 ml) was heated at 80° C. for 30 minutes. The cooled reaction mixture was purified ($SiO_2$, ethyl acetate:isohexane 1:4 as eluant) to afford the subtitle compound (0.44 g).

MS (APCI) 502/4 (M+H+), 504 (100%).

j) [3aR-[3aα,4α,6α(1R*,2S*),6aα]]-[[6-[7-[[2-(3,4-Difluorophenyl)cyclopropyl]amino]-5-(propylthio)-3H-1,2,3-triazolo[4,5-d]-pyrimidin-3-yl]-tetrahydro-2,2-dimethyl-4H-cyclopenta-1,3-dioxol-4-yl]oxy]acetic acid, methyl ester To a mixture of the products from step i) (0.80 g) and Example 2, step d) (0.61 g) in dichloromethane (25 ml) was added N,N-diisopropylethylamine (0.85 ml). The resulting solution was stirred at room temperature for 16 hours then concentrated in vacuo. Purification ($SiO_2$, isohexane:ethylacetate 3:1 as eluant) gave the subtitle compound as a colourless foam (0.77 g).

MS (APCI) 591 ($M+H^+$, 100%)

k)[3aR-[3aα,4α,6α(1R*,2S*),6aα]]-2-[6-[[7-[2-(3,4-Difluorophenyl)cyclopropyl]amino-5-(propylthio)-3H-1,2,3-triazolo[4,5-d]pyrimidin-3-yl]-tetrahydro-2,2-dimethyl-4H-cyclopenta-1,3-dioxol-4-yl]oxy]-ethanol DIBAL-H® (1.0M solution in hexanes, 5.15 ml) was added to an ice-cooled solution of the product of step j) (0.76 g) in tetrahydrofuran (1 ml) and the solution stirred at this temperature for 2 hours. The reaction mixture was concentrated in vacuo and the residue was dissolved in ethyl acetate (75 ml). A saturated aqueous solution of sodium potassium tartrate (75 ml) was added and the mixture stirred vigorously for 16 hours. The organics were collected and the aqueous re-extracted with ethyl acetate (2×50 ml). The combined organics were dried and concentrated and the residue purified ($SiO_2$, isohexane:ethylacetate 1:1 as eluant) to give the subtitle compound (0.63 g).

MS (APCI) 563 ($M+H^+$, 100%)

1)[1S-[1α,2α,3β(1S*,2R*),5β]]-3-[7-(2-(3,4-Difluorophenyl)cyclopropylamino)5-(propylthio)-3H-1,2,3-triazolo[4,5-d]pyrimidin-3-yl)-5-(2-hydroxyethoxy)-cyclopentane-1,2-diol Prepared according to the method of example 1, step h) using the product of step k).

MS (APCI) 523 ($M+H^+$, 100%)

NMR δH ($d_6$-DMSO) 8.95 (1H, d, J=3.3 Hz), 7.39-7.21 (2H, m), 7.10-7.00 (1H,m),5.12 (1H, d, J=6.4 Hz), 5.05 (1H, d, J=3.6 Hz), 4.96 (1H, q, J=9.0 Hz), 4.62-4.54 (2H,m),3.95 (1H, br s), 3.79-3.73 (1H, m), 3.55-3.47 (4H, m), 3.20-3.13 (1H, m), 2.98-2.81 (2H,m), 2.63 (1H, dt, J=13.6, 8.5 Hz), 2.29-2.21 and 2.16-2.09 (1H, m), 2.07-2.00 (1H,m), 1.73-1.33 (4H, m), 0.99 (3H, t, J=7.4 Hz).

Example 4

[1R-[1α,2α,3β(1R*,2S*),5β]]-3-[5-(Butylthio)-7-[[2-(3,4-difluorophenyl)cyclopropyl]amino]-3H-1,2,3-triazolo[4,5-d]pyrimidin-3-yl]-5-(hydroxymethyl)-cyclopentane-1,2-diol a) [3aR-(3aα,4α,6α,6aα)]-6-[7-Amino-5-(propylthio)-3H-1,2,3-triazolo[4,5-d]pyrimidin-3-yl]-tetrahydro-2,2-dimethyl-4H-cyclopenta-1,3-dioxole-4-methanol Prepared according to the method of Example 3, step g) using [3aR-(3aα,4α,6α,6aα)]-6-[7chloro-5-(propylthio)-3H-1,2,3-triazolo[4,5-d]pyrimidin-3-yl]-tetrahydro-2,2-dimethyl-4H-cyclopenta-1,3-dioxole-4-methanol (prepared as described in International Patent Application WO 9703084). The crude product was purified ($SiO_2$, methanol:dichloromethane 1:19 as eluant) to give the subtitle compound.

MS (APCI) 381 ($M+H^+$, 100%).

b) [3aR-(3aα,4α,6α,6aα)]-6-[7-Amino-5-(propylsulfonyl)-3H-1,2,3-triazolo[4,5-d]pyrimidin-3-yl]-tetrahydro-2,2-dimethyl-4H-cyclopenta-1,3-dioxole-4-methanol Prepared according to the method of example 1, step f) using the product of step a).

MS (APCI) 413 ($M+H^+$, 100%).

c) [3aR-(3aα,4α,6α,6aα)]-6-[7-Amino-5-(butylthio)-3H-1,2,3-triazolo[4,5-d]pyrimidin-3-yl]-tetrahydro-2,2-dimethyl-4H-cyclopenta-1,3-dioxole-4-methanol 1-Butanethiol (2.38 ml) in DMF (25 ml) was added to a suspension of sodium hydride (60%, 1.09 g) in DMF (50 ml). After 1 hour a solution of the product of step b) (3.66 g) in DMF (65 ml) was added dropwise and the resulting mixture was stirred overnight. The reaction mixture was added slowly to saturated aqueous sodium bicarbonate (1000 ml) and then extracted into ethyl acetate (3×200 ml). The organic phase was dried ($MgSO_4$) and concentrated in vacuo and the residue purified ($SiO_2$, methanol:dichloromethane 1:19 as eluant) to give the subtitle compound (3.32 g).

MS (APCI) 395 ($M+H^+$, 100%).

d) [3aR-(3aα,4α,6α,6aα)]-6-[7-Amino-5-(butylthio)-3H-1,2,3-triazolo[4,5d]pyrimidin-3-yl]-tetrahydro-2,2-dimethyl-4H-cyclopenta-1,3-dioxole-4-methanol, acetate To a solution of the product from step c) (3.3 g) in dichloromethane (50 ml), was added pyridine (2.7 ml), 4-dimethylaminopyridine (0.4 g) and acetic anhydride (2.0 ml). The mixture was stirred at room temperature overnight, concentrated in-vacuo and purified ($SiO_2$, diethyl ether: isohexane 3:2 as eluent) to give the subtitle compound (2.7 g).

MS (APCI) 437 ($M+H^+$, 100%).

e) [3aR-(3aα,4α,6α,6aα)]-6-[7-Bromo-5-(butylthio)-3H-1,2,3-triazolo[4,5-d]pyrimidin-3-yl]-tetrahydro-2,2-dimethyl-4H-cyclopenta-1,3-dioxole-4-methanol, acetate Prepared according to the method of example 3, step i) using the product of step d).

MS (APCI) 500/502 ($M+H^+$), 500 (100%).

f) [3aR-[3aα,4α,6α(1R*,2S*),6aα]]-6-[5-(Butylthio)-7-[[2-(3,4-difluorophenyl)cyclopropyl]amino]-3H-1,2,3-triazolo[4,5-d]pyrimidin-3-yl]-tetrahydro-2,2-dimethyl-4H-cyclopenta-1,3-dioxole-4-methanol, acetate Prepared according to the method of example 3, step j) using the product of example 2, step d) and the product of step e).

MS (APCI) 589 ($M+H^+$, 100%).

g) [1R-[1α,2α,3β(1R*,2S*),5β]]-3-[5-(Butylthio)-7-[[2-(3,4-difluorophenyl)cyclopropyl]amino]-3H-1,2,3-triazolo[4,5-d]pyrimidin-3-yl]-5-(hydroxymethyl)-cyclopentane-1,2-diol The product of step f) (0.64 g) in 80% aqueous acetic acid (30 ml) was heated at 80° C. for 1 hour. The cooled mixture was poured into saturated sodium bicarbonate solution and extracted into ethyl acetate. The organic phase was dried and concentrated in vacuo to give a gum which was dissolved in methanol (50 ml)/10% aqueous potassium carbonate solution (3 ml). The solution was stirred for 30 minutes, neutralised with acetic acid, and concentrated in vacuo. Purification ($SiO_2$, methanol:dichloromethane 1:19 as eluent) gave a solid which was recrystallised (acetonitrile) to give the title compound (0.25 g).

MS (APCI) 507 ($M+H^+$, 100%).

NMR δH ($d_6$DMSO) 9.34 (1H, br), 7.40-7.23 (2H, m), 7.11-7.00 (1H, m), 5.06-4.93 (2H, m), 4.76-4.67 (2H, m), 4.48-4.38 (1H, m), 3.91-3.84 (1H, m), 3.56-3.39 (2H, m), 3.21-3.08 (1H, m), 3.03-2.83 (2H, m), 2.32-2.17 (1H, m), 2.17-2.03 (2H, m), 1.91-1.77 (1H, m), 1.71-1.32 (4H, m), 1.32-1.17 (2H, m), 0.81 (3H, t).

Example 5

[1S-[1α,2β,3β,4α(1S*,2R*)]]-4-[5-(Butylthio)7-[[2-(4-fluorophenyl)cyclopropyl]amino]-3H-1,2,3-triazolo[4,5-d]pyrimidin-3-yl]-cyclopentane-1,2,3-triol a) [3aR-[3aα,4α,6α,6aα(1S*,2R*)]]-6-[7-[[(4-Fluorophenyl)cyclopropyl]amino]-5-(propylthio)-3H-1,2,3-triazolo[4,5-d]pyrimidin-3-yl]-tetrahydro-2,2-dimethyl-4H-cyclopenta-1,3-dioxol-4-ol Prepared according to the method of example 1, step e) using the product of example 1, step d) and the product of example 3 step f).

MS (APCI) 501 ($M+H^+$, 100%).

b) [3aR-[3aα,4α,6α,6aα(1S*,2R*)]]-6-[[7-[(4-Fluorophenyl)cyclopropyl]amino]-5-(propylsulphonyl)-3H-1,2,3-triazolo[4,5-d]pyrimidin-3-yl]-tetrahydro-2,2-dimethyl-4H-cyclopenta-1,3-dioxol-4-ol Prepared according to the method of example 1, step f) using the product of step a).

MS (APCI) 532 ($M+H^+$, 100%).

c) [3aR-[3aα,4α,6α,6aα(1S*,2R*)]]-6-[7-[[(4-Fluorophenyl)cyclopropyl]amino]-5-(butylthio)-3H-1,2,3-triazolo[4,5-d]pyrimidin-3-yl]-tetrahydro-2,2-dimethyl-4H-cyclopenta-1,3-dioxol-4-ol Prepared according to the method of example 4 step c) using the product of step b).

MS (APCI) 515 ($M+H^+$, 100%).

[1S-[1α,2β,3β,4α(1S*,2R*)]]-4-[S-(Butylthio)-7-[[2-(4-fluorophenyl)cyclopropyl]amino]-3H-1,2,3-triazolo[4,5-d]pyrimidin-3-yl]-cyclopentane-1,2,3-triol Prepared according to the method of example 1 step h) using the product of step c).

MS (APCI) 575 ($M+H^+$, 100%).

NMR δH ($d_6$-DMSO) 7.26-7.22 (2H, m), 7.11 (2H, t), 4.99-4.90 (1H, m), 4.67-4.63 (1H, m), 3.93 (1H, s), 3.77 (1H, bs), 3.35-3.13 (1H, m), 3.00-2.80 (2H, m), 2.59-2.51 (1H, m), 2.15-2.11 (1H, m), 1.91-1.86 (1H, m), 1.53-1.41 (3H, m), 1.35-1.30 (1H, m), 1.22 (2H, sex), 0.80 (3H, t).

Example 6

[1S-[1α,2α,3β(1S*,2R*),5β)]-3-[7-[[2-(3,4-Difluorophenyl)cyclopropyl]amino]-5-[(3,3,3-trifluoropropyl)thio]-3H-1,2,3-triazolo[4,5-d]pyrimidin-3-yl]-5-(2-hydroxyethoxy)-cyclopentane-1,2-diol a) [1S-(1α,2α,3β(1S*,2R*),5β)]-3-[7-[[2-(3,4-Difluorophenyl)cyclopropyl]amino]-5-(propylsulphonyl)-3H-1,2,3-triazolo[4,5-d]pyrimidin-3-yl)-5-(2-hydroxyethoxy)-cyclopentane-1,2-diol The subtitle compound was prepared according to the method of Example 1, step f) using the product of Example 3, step 1.

MS(APCI) 555($M+H^+$, 100%)

b) [1S-(1α,2α,3β(1S*,2R*),5β)]-3-[7-[[2-(3,4-Difluorophenyl)cyclopropyl[amino]-5-[(3,3,3-trifluoropropyl)thio]-3H-1,2,3-triazolo[4,5-d]pyrimidin-3-yl)-5-(2-hydroxyethoxy)-cyclopentane-1,2-diol The title compound was prepared according to the method of Example 1, step g) using the product of step a).

MS(APCI) 555 ($M+H^+$, 100%)

NMR δH ($d_6$-DMSO) 9.45 (1H, d), 7.36-7.05 (3H, m), 5.05 (1H, d), 5.02 (1H, d), 4.95 (1H, m), 4.60 (2H, m), 3.95 (1H, m), 3.86 (1H, m), 3.47 (4H, m), 3.30-3.11 (3H, m), 2.63-2.49 (3H, m), 2.19 (1H, m), 2.00 (1H, m), 1.53 (1H, m), 1.40 (1H, m).

Example 7

[1S-[1α,2α,3β,5β(1S*,2R*)]]-3-(2Hydroxyethoxy)-5-[7-(2-phenylcyclopropyl)amino]-5-[(3,3,3-trifluoropropyl)thio]-3H-1,2,3-triazolo[4,5-d]pyrimidin-3-yl]-cyclopentane-1,2-diol a) (1S-cis)-2-[[4-[[6-Chloro-5-nitro-2-[(3,3,3-trifluoropropyl)thio]-4-pyrimidinyl]amino]-2-cyclopenten-1-yl]oxy]-acetic acid, ethyl ester A solution of sodium azide (4.70 g) in degassed water (25 ml) was added to a solution of (1R,4S)-4-hydroxy-2-cyclopenten-1-yl acetate (9.99 g) in tetrahydrofuran (60 ml) and stirred for 10 min. Tetrakis(triphenylphosphine) palladium (0) (365 mg) was added and stirred for 10 min. The aqueous layer was separated and extracted twice with ethyl acetate. The combined organic layers were dried ($MgSO_4$), concentrated and purified on a short column ($SiO_2$, ethyl acetate: isohexane 1:2 as eluant) to afford a yellow oil. This was dissolved in tetrahydrofuran (25 ml) and slowly added to a suspension of sodium hydride (2.94 g, 60% dispersion in oil) in tetrahydrofuran (60 ml) at −78° C. A solution of ethyl bromoacetate (8.2 ml) in tetrahydrofuran (5 ml) was added and the mixture was allowed to warm to 20° C. and stirred for 30 min. Aqueous ammonium chloride solution was added and the mixture was extracted with ether. The organic layers were dried ($MgSO_4$), concentrated and purified ($SiO_2$, ether:isohexane 1:5 as eluant) to afford a colourless oil. A solution of this oil and triphenylphosphine (17.89 g) in tetrahydrofuran (90 ml) was stirred for 10 min. Water (15 ml) was added and the solution was stirred for 18 hours. The solvent was removed in vacuo and the residue azeotroped with toluene then purified ($SiO_2$, ethyl acetate then ethyl acetate-methanol-ammonia (90:9:1) as eluant) to afford a pale yellow oil (7.14 g).

A solution of this compound in tetrahydrofuran (50 ml) was added over 25 min to a solution of 4,6-dichloro-5-nitro-2-[(3,3,3-trifluoropropyl)thio]pyrimidine (prepared as described in International Patent Application WO 9703084) (24.8 g) and N,N-diisopropylethylamine (77.5 ml) in dry tetrahydrofuran (100 ml) and then stirred for 30 minutes. Water was added and the mixture was extracted with ether (three times). The organic layers were dried ($MgSO_4$), concentrated and purified ($SiO_2$, ethyl acetate:isohexane 1:4 as eluant) to afford the subtitle compound (7.39 g).

MS (APCI) 36719 (M-($EtO_2CCH_2O$)$^+$), 367 (100%)

b) (1S-cis)2-[[4-[7-Chloro-5-[(3,3,3-trifluoropropyl)thio]-3H-1,2,3-triazolo[4,5-d]-pyrimidin-3-yl]-2-cyclopenten-1-yl]oxy]-acetic acid, ethyl ester Prepared according to the method of example 3, steps e) and f) using the product of step a).

MS (APCI) 348/50 (M-($EtO_2CCH_2O$)$^+$), 348 (100%).

c) [1S-(cis)]2-[[4-[7-Amino-5-[(3,3,3-trifluoropropyl)thio]-3H-1,2,3triazolo[4,5-d]pyrimidin-3-yl]-2-cyclopenten-1-yl]oxy]-acetic acid, ethyl ester Prepared according to the method of example 3, step g) using the product of step b).

MS (APCI) 433 (M+H$^+$, 100%).

d) [1S-(cis)]2-[[4-[7-Amino-5-[(3,3,3-trifluoropropyl)thiol-3H-1,2,3-triazolo[4,5-d]pyrimidin-3-yl]-2-cyclopenten-1-yl]oxy]-1-ethanol Prepared according to the method of example 3, step k) using the product of step c).

MS (APCI) 391 (M+H$^+$, 100%).

e) [3aR-(3aα,4α,6α,6aα)]-2-[6-[7-Amino-5-[(3,3,3-trifluoropropyl)thio]-3H-1,2,3-triazolo[4,5-d]-pyrimidin-3-yl]-tetrahydro-2,2-dimethyl-4H-cyclopenta-1,3-dioxol-4-yloxy]ethanol A solution of the product from step d) (454 mg), osmium tetroxide (0.17 ml of 0.1M solution in t-butanol), N-methylmorpholine N-oxide (210 mg) and pyridine (0.09 ml) in acetone (5 ml) and water (1 ml) was heated at 70° C. for 5 hours. Sodium hydrosulfite (330 mg) in water (1 ml) was added, the solvent was remove in vacuo and the residue azeotroped with toluene. A solution of this and p-toluenesulfonic acid (50 mg) in acetone (5 ml) and 2,2-dimethoxypropane (2 ml) was stirred for 3 h. The solvent was remove in vacuo, aq sodium hydrogen carbonate solution added and the mixture was extracted with ethyl acetate. The organic layers were dried ($MgSO_4$), concentrated and purified ($SiO_2$, isohexane:acetone 5:2 as eluant) to afford the subtitle compound as a white solid (367 mg).

MS (APCI) 465 (M+H$^+$, 100%)

f) [3aR-[3aα,4α,6α,6aα)]-2-[6-[7-Bromo-5-[(3,3,3-trifluoropropyl)thio]-3H-1,2,3-triazolo[4,5 d]-pyrimidin-3-yl]-tetrahydro-2,2-dimethyl-4H-cyclopenta-1,3-dioxol-4-yloxy]ethanol Prepared according to the method of Example 3, step i) using the product of step e).

MS (APCI) 528130 (M+H$^+$), 528 (100%)

g) [3-[3aα,4α,6α(1R*,2S*),6aα]-2-[6-(7-Phenylcyclopropyl)amino]-5-[(3,3,3-trifluoropropyl)thio]-3H-1,2,3-triazolo[4,5-d]pyrimidin-3-yl]-tetrahydro-2,2-dimethyl-4H-1,3-dioxol-4-yloxy]ethanol Prepared according to the method of Example 3, step j) using the product of step f) and (1R-trans)-2-phenylcyclopropanamine, [R-(R*,R*)]-2,3-dihydroxybutanedioate (1:1) (prepared as described by L. A. Mitscher et al., J. Med. Chem. 1986, 29, 2044).

MS (APCI) 581 (M+H$^+$, 100%)

h) [1S-[1α,2α,3β,5β(1S*,2R*)]]-3-(2Hydroxyethoxy)-5-[7-(2-phenylcyclopropyl)amino]-5-[(3,3,3-trifluoropropyl) thio]-3H-1,2,3-triazolo[4,5-d]pyrimidin-3-yl]-cyclopentane-1,2-diol Prepared according to the method of Example 1, step h) using the product of step g).

MS (APCI) 540 (M+H$^+$, 100%).

NMR δH ($d_6$-DMSO) 7.35-7.16 (5H, m), 4.97 (1H, q), 4.62-4.54 (1H, m), 3.98-3.92 (1H, m), 3.78-3.72 (1H, m), 3.55-3.44 (4H, m), 3.26-3.19 (2H, m), 3.16-3.07 (1H, m), 2.70-2.61 (1H, m), 2.58-2.52 (1H, m), 2.23-2.18 (1H, m), 2.05-1.97 (1H, m), 1.86 (1H, s), 1.54-1.46 (1H, m), 1.38-1.30 (1H, m).

Example 8

[1S-[1α,2β,3β,4α(1S*, 2R*)]]-4-[5-(Butylthio)-7-[[2-(3,4-difluorophenyl)cyclopropyl]amino]-3H-1,2,3-triazolo[4,5-d]pyrimidin-3-yl]cyclopentane-1,2,3-triol a) [3aR-[3aα,4α,6α(1R*,2S*),6aα]-6-[[7-[(3,4-Difluorophenyl)cyclopropyl]amino]-5-(propylthio)-3H-1,2,3-triazolo[4,5-d]pyrimidin-3-yl]-tetrahydro-2,2-dimethyl-4H-cyclopenta-1,3-dioxol-4-ol The subtitle compound was prepared according to the method of Example 1, step e) using the product of Example 3, step f) and the product of example 2, step d).

MS (APCI) 519 (M+H$^+$, 100%).

b) [3aR-[3aα,4α,6α(1R*,2S*),6aα]]-6-[[7-[(3,4-Difluorophenyl)cyclopropyl]amino]-5-(propylsulfonyl)-3H-1,2,3-triazolo[4,5-d]pyrimidin-3-yl]-tetrahydro-2,2-dimethyl-4H-cyclopenta-1,3-dioxol-4-ol The subtitle compound was prepared according to the method of Example 1, step f) using the product of step a).

MS (APCI) 551 (M+H$^+$, 100%).

c) [3aR-[3aα,4α,6α(1R*,2S*),6aα]]-6-[5-(Butylthio)-7-[[2-(3,4-difluorophenyl)cyclopropyl]amino]-3H-1,2,3-triazolo[4,5-d]pyrimidin-3-yl]-tetrahydro-2,2-dimethyl-4H-cyclopenta-1,3-dioxol-4-ol The subtitle compound was prepared according to the method of Example 4, step c) using the product of step b).

MS (APCI) 533 (M+H$^+$, 100%)

d) [1S-[1α,2β,3β,4α(1S*, 2R*)]]-4-[5-(Butylthio)-7-[[2-(3,4-difluorophenyl)cyclopropyl]amino]-3H-1,2,3-triazolo[4,5-d]pyrimidin-3-yl]cyclopentane-1,2,3-triol The title compound was prepared according to the method of Example 1, step h) using the product of step c).

NMR δH ($d_6$-DMSO) 7.15-6.98 (3H, m), 6.67 (1H, s), 5.11-5.09 (1H, m), 4.82-4.76 (1H m), 4.34-4.21 (3H, m), 3.7 (1H, s), 3.2-2.92 (4H, m), 2.77 (1H, m), 2.42-2.36 (1H, m), 2.2-2.18 (1H, m), 1.42-1.25 (6H, m), 0.9 (3H, q).

MS (APCI) 493 ($M+H^+$, 100%)

Example 9

[1S-[1α,2α,3β(1S*,2R2*),5β]]-3-[5-(Butylthio)-7-[(2-phenylcyclopropyl)amino]-3H-1,2,3-triazolo[4,5-d]pyrimidin-3-yl]-5-(2-hydroxethoxy)-cyclopentane-1,2-diol a) [3aS-(3aα,4α,6α,6aα)]-[Tetrahydro-6-hydroxy-2,2-dimethyl-4H-cyclopenta-1,3-dioxol-4-yl]-carbamic acid, phenylmethyl ester Potassium carbonate (39.3 g) was added to a suspension of [3αR-(3aα,4α,6α,6aα)]-6-amino-tetrahydro-2,2-dimethyl-4H-cyclopenta-1,3-dioxol-4-ol, hydrochloride, (prepared as described in WO 9905142) (27.1 g) in 4-methyl-2-pentanone (500 ml). Water (150 ml) was then added followed by dropwise addition of benzyl chloroformate (23.1 g). The reaction mixture was stirred at room temperature for 4 hours before the organic phase was separated. The aqueous phase was extracted with 4-methyl-2-pentanone (2×50 ml). The combined organics were concentrated and the residue was purified ($SiO_2$, dichloromethane:methanol, 95:5 to 90:10 as eluant) to give the subtitle compound (39.23 g).

NMR δH ($CDCl_3$) 7.32 (5H, m), 5.65 (1H, br s), 5.10 (2H, br s), 4.59 (1H, d), 4.48 (1H, d), 4.27 (1H, m), 4.19 (1H, br m), 2.24 (1H, br s), 1.69 (1H, d), 1.41 (3H, s), 1.26 (3H, s).

b) [3aS-(3aα,4α,6α,6aα)]-[2,2-Dimethyl-6-(2-hydroxyethoxy)-tetrahydro-4H-cyclopenta-1,3-dioxol-4-yl]-carbamic acid, phenylmethyl ester Potassium tert-butoxide (3.6 g) in tetrahydrofuran (20 ml) was added over 5 minutes to a solution of the product from step a) (39.23 g) in tetrahydrofuran (200 ml). After 15 minutes, ethyl bromoacetate (3.7 ml) in tetrahydrofuran (10 ml) was added dropwise. The mixture was stirred at 0° C. for 10 minutes, then further ethyl bromoacetate was added (3.7 ml×4).

The reaction mixture was stirred at 0° C. a further 2 hours. Lithium borohydride (2.79 g) was then added portionwise to the resulting suspension and the reaction mixture was stirred at <5° C. for 16 hours. Glacial acetic acid (23 g) was added dropwise to the cold mixture. After stirring for 30 minutes, water (100 ml) was added dropwise and the resulting mixture was stirred for 30 minutes. The phases were then separated and the aqueous phase was extracted with ethyl acetate. The combined organics were washed with saturated sodium bicarbonate and brine, dried and concentrated. The residue was purified ($SiO_2$, ethyl acetate:hexane, 25:75 to 50:50 as eluant) to give the subtitle compound (38.6 g).

MS (APCI) 218 ($M+H^+$, 100%).

c)) [3aR-(3aα,4α,6α,6aα)]-2-[[6-Amino-2,2-dimethyl-tetrahydro-4H-cyclopenta-1,3-dioxol-4-yl]oxy]-ethanol A slurry of 5% palladium on charcoal (4 g) in ethanol was added to a solution of the product from step b) (39.96 g) in ethanol (250 ml) and the mixture was hydrogenated at 1.2 bar for 20 hours. The catalyst was filtered off and the filtrate was concentrated to give the subtitle compound (23.65 g).

MS (APCI) 160 ($M+H^+$, 100%).

d) 2-(Butylthio)-4,6-dichloropyrimidine-5-amine

The subtitle compound was prepared according to the method of example 3, step e) using 2-(butylthio)-4,6-dichloro-5-nitro-pyrimidine (prepared as described in DE 2223644).

NMR δH ($CDCl_3$) 4.20 (2H, br s), 3.10 (2H, t), 1.70 (2H, m), 1.47 (2H, m), 0.95 (3H, t).

e) (3aR-(3aα,4α,6α,6aα)]-2-[[6-[[S-Amino-2-(butylthio)-6-chloro-pyrimidin-4-yl]amino]-tetrahydro-2,2-dimethyl4H-cyclopenta-1,3-dioxol-4-yl]oxy]ethanol The subtitle compound was prepared according to the method of example 3, step d) using the products of steps c) and d).

MS (APCI) 433 ($M+H^+$, 100%).

f) [3aR-[3aα,4α,6α(1R*,2S*),6aα]]-2-[6-[[5-(Butylthio)-7-chloro-3H-1,2,3-trizolo[4,5-d]pyrimidin-3-yl]-tetrahydro-2,2-dimethyl-4H-cyclopenta-1 ,3-dioxol-4-yl] oxy]-ethanol The subtitle compound was prepared according to the method of Example 3, step f) using the product of step e).

NMR δH ($CDCl_3$) 5.53 (1H, m), 5.21 (1H, m), 4.88 (1H, d), 4.05 (1H, m), 3.59 (4H, m), 3.24 (2H, t), 2.70 (1H, m), 2.53 (1H, m), 2.13 (1H, t), 1.79 (2H, m), 1.55 (5H, m), 1.37 (3H, s), 0.98 (3H, t).

g) [3aR-[3aα,4α,6α(1R*,2S*),6aα]-2-[6-[[5-(Butylthio)-7-[2-phenylcyclopropyl]amino-3H-1,2,3-triazolo[4,5-d]pyrimidin-3-yl]-tetrahydro-2,2-dimethyl-4H-cyclopenta-1,3-dioxol-4-yl]oxy]-ethanol The subtitle compound was prepared according to the method of Example 3, step j) using the product of step f).

MS (APCI) 541 ($M+H^+$, 100%).

h) [1S-[1α,2α,3β(1S*,2R*),5β]]-3-[5-(Butylthio)-7-[(2-phenylcyclopropyl)amino]-3H-1,2,3-triazolo[4,5-d]pyrimidin-3-yl]-5-(2-hydroxethoxy)-cyclopentane-1,2-diol The title compound was prepared according to the method of example 1, step h) using the product of step g).

MS (APCI) 501 ($M+H^+$, 100%)

NMR δH ($d_6$-DMSO) 9.33 (1H, d), 7.30 (2H, m), 7.18 (3H, m), 5.12 (1H, d), 5.04 (1H, d), 4.96 (1H, q), 4.59 (2H, m), 3.94 (1H, s), 3.76 (1H, m), 3.51 (4H, m), 3.22 (1H, m), 2.98 (1H, m), 2.86 (1H, m), 2.65 (1H, m), 2.14 (1H, m), 2.05 (1H, m), 1.21-1.53 (6H, m), 0.80 (3H, t).

Pharmacological Data

The preparation for the assay of the $P_{2T}$ ($P2Y_{ADP}$ or $P2T_{AC}$) receptor agonist/antagonist activity in washed human platelets for the compounds of the invention was carried out as follows.

Human venous blood (100 ml) was divided equally between 3 tubes, each containing 3.2% trisodium citrate (4 ml) as anti-coagulant. The tubes were centrifuged for 15 minutes at 240 G to obtain a platelet-rich plasma (PRP) to which 300 ng/ml prostacyclin was added to stabilize the platelets during the washing procedure. Red cell free PRP was obtained by centrifugation for 10 minutes at 125G followed by further centrifugation for 15 minutes at 640 G. The supernatant was discarded and the platelet pellet resuspended in modified, Calcium Free Tyrode solution (10 ml) (CFT), composition: NaCl 137 mM, $NaHCO_3$ 11.9 mM, $NaH_2PO_4$ 0.4 mM, KCl 2.7 mM, $MgCl_2$ 1.1 mM, dextrose 5.6 mM, gassed with 95% $O_2$/5% $CO_2$ and maintained at 37° C. Following addition of a further 300 ng/ml $PGI_2$, the pooled suspension was centrifuged once more for 15 minutes at 640 G. The supernatant was discarded and the platelets resuspended initially in 10 ml CFT with further CFT added to adjust the final platelet count to $2\times10^5$/ml. This final suspension was stored in a 60 ml syringe at 3° C. with air excluded. To allow recovery from $PGI_2$-inhibition of normal function, platelets were used in aggregation studies no sooner than 2 hours after final resuspension.

In all studies, 3 ml aliquots of platelet suspension were added to tubes containing $CaCl_2$ solution (60 μl of 50 mM solution with a final concentration of 1 mM). Human fibrinogen (Sigma, F 4883) and 8-sulphophenyltheophylline (8-SPT which was used to block any $P_1$-agonist activity of compounds) were added to give final concentrations of 0.2 mg/ml (60 μl of 10 mg/ml solution of clottable protein in saline) and 300 nM (10 μl of 15 mM solution in 6% glucose), respectively. Platelets or buffer as appropriate were added in a volume of 150 μl to the individual wells of a 96 well plate. All measurements were made in triplicate in platelets from each donor.

The agonist/antagonist potency was assessed as follows.

Aggregation responses in 96 well plates were measured using the change in absorbance given by the plate reader at 660 nm. Either a Bio-Tec Ceres 900C or a Dynatech MRX were used as the plate reader.

The absorbance of each well in the plate was read at 660 nm to establish a baseline figure. Saline or the appropriate solution of test compound was added to each well in a volume of 10 μl to give a final concentration of 0, 0.01, 0.1, 1, 10 or 100 mM. The plate was then shaken for 5 min on an orbital shaker on setting 10 and the absorbance read at 660 nm. Aggregation at this point was indicative of agonist activity of the test compound. Saline or ADP (30 mM; 10 μl of 450 mM) was then added to each well and the plate shaken for a further 5 min before reading the absorbance again at 660 nm.

Antagonist potency was estimated as a % inhibition of the control ADP response to obtain an $IC_{50}$. Compounds exemplified have $pIC_{50}$ values of more than 5.0.

What is claimed is:

1. A compound of formula (I)

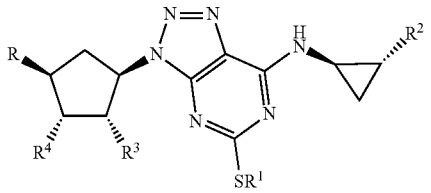

wherein:

$R^1$ is $C_{3-5}$ alkyl optionally substituted by one or more halogen atoms;

$R^2$ is a phenyl group, optionally substituted by one or more fluorine atoms;

$R^3$ and $R^4$ are both hydroxy;

R is XOH, where X is $CH_2$, $OCH_2CH_2$ or a bond;

or a pharmaceutically acceptable salt or solvate thereof, or a solvate of such a salt provided that:

when X is $CH_2$ or a bond, $R^1$ is not propyl;

when X is $CH_2$ and $R^1$ is $CH_2CH_2CF_3$, butyl or pentyl, the phenyl group at $R^2$ must be substituted by fluorine;

when X is $OCH_2CH_2$ and $R^1$ is propyl, the phenyl group at $R^2$ must be substituted by fluorine.

2. A compound according to claim 1 in which $R^1$ is 3,3,3[,]-trifluoropropyl, butyl or propyl.

3. A compound according to claim 1 in which $R^2$ is phenyl or 4-fluorophenyl or 3,4-difluorophenyl.

4. A compound according to claim 1 in which R is $CH_2OH$ or $OCH_2CH_2OH$.

5. A compound according to claim 1 which is:

[1R-[1α,2α,3β(1R*,2S*),5β]]-3-[7-[[2-(4-Fluorophenyl)cyclopropyl]amino]-5-[(3,3,3-trifluoropropyl)thio]-3H-1,2,3-triazolo[4,5-d]pyrimidin-3-yl]-5-(hydroxymethyl)-cyclopentane-1,2-diol;

[1R-[1α,2α,3β(1R*,2S*),5β]]-3-[7-[[2-(3,4-Difluorophenyl)cyclopropyl]amino]-5-[(3,3,3-trifluoropropyl)thio]-3H-1,2,3-triazolo[4,5-d]pyrimidin-3-yl]-5-(hydroxymethyl)-cyclopentane-1,2-diol;

[[1S-(1α,2α,3β(1S*,2R*),5β]]]*[1S-[1α,2α,3β(1S*,2R*),5β]]*-3-[7-[[2-(3,4-Difluorophenyl)cyclopropyl]amino]-5-(propylthio)-3H-1,2,3-triazolo[4,5-d]pyrimidin-3-yl]-5-(2-hydroxyethoxy)-cyclopentane-1,2-diol;

1R-[1α,2α,3β(1R*,2S*),5β]]-3-[5-(Butylthio)-7-[[2-(3,4-difluorophenyl)cyclopropyl]amino]-3H-1,2,3-triazolo[4,5-d]pyrimidin-3-yl]-5-(hydroxymethyl)-cyclopentane-1,2-diol;

[1S-[1α,2β,3β,4α(1S*,2R*)]]-4-[5-(Butylthio)-[7-[[2-(4-flurophenyl)cyclopropyl]amino]]*7-[[2-(4-fluorophenyl)cyclopropyl]amino]*-3H-1,2,3-triazolo[4,5-d]pyrimidin-3-yl]-cyclopentane-1,2,3-triol;

[1S-(1α,2α,3β(1S*,2R*),5β]-3-[7-[[2-(3,4-Difluorophenyl)cyclopropyl]amino]-5-[(3,3,3-trifluoropropyl)thio]-3H-1,2,3-triazolo[4,5-d]pyrimidin-3-yl]-5-(2-hydroxyethoxy)-cyclopentane-1,2-diol;

[1S-[1α,2α,3β,5β(1S*,2R*)]]-3-(2-Hydroxyethoxy)-5-[7-(2-phenylcyclopropyl)amino]-5-[(3,3,3-trifluoropropyl)thio]-3H-1,2,3-triazolo[4,5-d]pyrimidin-3-yl]-cyclopentane-1,2-diol [1S-[1α,2β,3β,4α(1S*,2R*)]]-4-[5-(Butylthio)-7-[[2-(3,4-difluorophenyl)cyclopropyl]amino]-3H-1,2,3-triazolo[4,5-d]pyrimidin-3-yl]cyclopentane-1,2,3-triol;

[1S-[1α,2α,3β(1S*,2R*),5β]]-3-[5-(Butylthio)-7-[(2-phenylcyclopropyl)amino]-3H-1,2,3-triazolo[4,5-d]pyrimidin-3-yl]-5-(2-hydroxethoxy)-cyclopentane-1,2-diol;

or pharmaceutically acceptable salts or solvates thereof, or solvates of such salts.

6. A pharmaceutical composition comprising a compound according to claim 1 in combination with a pharmaceutically acceptable diluent, [adjuvent] *adjuvant* and/or carrier.

7. A method of treatment of post-myocardial infarction which comprises administering to a patient suffering therefrom a therapeutically effective amount of a compound according to claim 1.

8. A process for the preparation of a compound of formula (I) which comprises reacting a compound of formula (II):

(II)

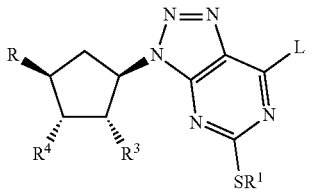

where R, $R^1$, $R^3$ and $R^4$ are as defined in claim 1, or are protected derivatives thereof, or $R^3$ and $R^4$ together form a bond in the 5-membered ring, or R is $CH_2CH_2OR'$ where R' is $C_{1-6}$ alkyl or benzyl, and L is a leaving group, with a compound of formula (III):

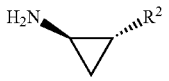

(III)

where $R^2$ is defined in claim 1 or is a protected derivative thereof, in the presence of a base in an inert solvent at ambient or elevated temperature, and optionally thereafter and in any order:

converting one or more functional groups into further functional groups;

removing any protecting groups;

forming a pharmaceutically acceptable salt or solvate, or a solvate of such a salt.

9. The compounds:

[3aR-[3aα,4α,6α(1R*,2S*),6aα]]-6-[7-[[2-(4-Fluorophenyl)cyclopropyl]amino]-5-(propylsulphonyl)-3H-1,2,3-triazolo[4,5-d]pyrimidin-3-yl]-tetrahydro-2,2-dimethyl-4H-cyclopenta-1,3-dioxole-4-methanol;

[[[3aR-[3aα,4α,6α(1R*,2S*),6aα]]]*[3aR-[3aα,4α,6α(1R*,2S*),6aα]]*-6-[7-[[2-(4-Fluorophenyl)cyclopropyl]amino]-5-[(3,3,3-trifluoropropy)lthio]-3H-1,2,3-[triazolo[4,5-d]pyrimidin-3-yl)]*triazolo[4,5-d]pyrimidin-3-yl]*-tetrahydro-2,2-dimethyl-4H-cyclopenta-1,3-dioxole-4-methanol;

[3aR-[3aα,4α,6α(1R*,2S*),6aα]-6-[7-[[2-(3,4-Difluorophenyl)cyclopropyl]amino]-5-[(3,3,3-trifluoropropyl)thio]-3H-1,2,3-triazolo[4,5-d]pyrimidin-3-yl]-tetrahydro-2,2-dimethyl-4H-cyclopenta-1,3-dioxole-4-methanol;

[3aR-(3aα,4α,6α,6aα)]-6-[7-Amino-5-(propylthio)-3H-1,2,3-triazolo[4,5-d]-pyrimidin-3-yl]-tetrahydro-2,2-dimethyl-4H-cyclopenta-1,3-dioxol-4-ol;

[3aR-(3aα,4α,6α,6aα)]-[[6-[7-Amino-5-(propylthio)-3H-1,2,3-triazolo[4,5-d]-pyrimidin-3-yl]-tetrahydro-2,2-dimethyl-4H-cyclopenta-1,3-dioxol-4-ol]oxy]acetic acid, methyl ester; *or*

[3aR-(3aα,4α,6α,6aα)]-[[6-[7-Bromo-5-(propylthio)-3H-1,2,3-triazolo[4,5-d]-pyrimidin-3-yl]-tetrahydro-2,2-dimethyl-4H-cyclopenta-1,3-dioxol-4-ol]oxy]acetic acid, methyl ester.

10. The compounds:

[3aR-[3aα,4α,6α(1R*,2S*),6aα]]-[[6-[7-[[2-(3,4-Difluorophenyl)cyclopropyl]amino]-5-(propylthio)-3H-1,2,3-triazolo[4,5-d]-pyrimidin-3-yl]-tetrahydro-2,2-dimethyl-4H-cyclopenta-1,3-dioxol-4-yl]oxy]acetic acid, methyl ester;

[3aR-[3aα,4α,6α(1R*,2S*),6aα]]-6-[[7-[2-(3,4-Difluorophenyl)cyclopropyl]amino-5-(propylthio)-3H-1,2,3-triazolo[4,5-d]pyrimidin-3-yl]-tetrahydro-2,2-dimethyl-4H-cyclopenta-1,3-dioxol-4-yl]oxy]-ethanol;

[3aR-(3aα,4α,6α,6aα)]-6-[7-Amino-5-(propylthio)-3H-1,2,3-triazolo[4,5-d]pyrimidin-3-yl]-tetrahydro-2,2-dimethyl-4H-cyclopenta-1,3-dioxole-4-methanol; *or*

[3aR-(3aα,4α,6aα)]-6-[7-Amino-5-(propylsulfonyl)-3H-1,2,3-triazolo[4,5-d]pyrimidin-3-yl]-tetrahydro-2,2-dimethyl-4H-cyclopenta-1,3-dioxole-4-methanol[;].

11. The compounds:

[3aR-(3aα,4α,6α,6aα)]-6-[7-Amino-5-(butylthio)-3H-1,2,3-triazolo[4,5-d]pyrimidin-3-yl]-tetrahydro-2,2-dimethyl-4H-cyclopenta-1,3-dioxole-4-methanol;

[3aR-(3aα,4α,6α,6aα)]-6-[7-Amino-5-(butylthio)-3H-1,2,3-triazolo[4,5-d]pyrimidin-3-yl]-tetrahydro-2,2-dimethyl-4H-cyclopenta-1,3-dioxole-4-methanol, acetate;

[3aR-(3aα,4α,6α,6aα)]-6-[7-Bromo-5-(butylthio)-3H-1,2,3-triazolo[4,5-d]pyrimidin-3-yl]-tetrahydro-2,2-dimethyl-4H-cyclopenta-1,3-dioxole-4-methanol, acetate;

[3aR-[3aα,4α,6α(1R*,2S*),6aα]]-6-[5-(Butylthio)-7-[[2-(3,4-difluorophenyl)cyclopropyl]amino]-3H-1,2,3-triazolo[4,5-d]pyrimidin-3-yl]-tetrahydro-2,2-dimethyl-4H-cyclopenta-1,3-dioxole-4-methanol, acetate;

[3aR-[3aα,4α,6α,6aα(1S*,2R*)]]-6-[7-[[(4-Fluorophenyl)cyclopropyl]amino]-5-(propylthio)-3H-1,2,3-triazolo[4,5-d]pyrimdin-3-yl]-tetrahydro-2,2-dimethyl-4H-cyclopenta-1,3-dioxol-4-ol; *or*

[3aR-[3aα,4α,6α,6aα(1S*,2R*)]]-6-[[7-[(4-Fluorophenyl)cyclopropyl]amino]-5-(propylsulphonyl)-3H-1,2,3-triazolo[4,5-d]pyrimidin-3-yl]-tetrahydro-2,2-dimethyl-4H-cyclopenta-1,3-dioxol-4-ol[;].

12. The compounds:

[3aR-[3aα,4α,6α,6aα(1S*,2R*)]]-6-[7-[[(4-Fluorophenyl)cyclopropyl]amino]-5-(butylthio)-3H-1,2,3-triazolo[4,5-d]pyrimidin-3-yl]-tetrahydro-2,2-dimethyl-4H-cyclopenta-1,3-dioxol-4-ol;

[1S-(1α,2α,3β(1S*,2R*),5β)]-3-[7-[[2-(3,4-Difluorophenyl)cyclopropyl]amino]-5-(propylsulphonyl)-3H-1,2,3-triazolo[4,5-d]pyrimidin-3-yl)-5-(2-hydroxyethoxy)-cyclopentane-1,2-diol;

(1S-cis) 2-[[4-[7-Chloro-5-[(3,3,3-trifluoropropyl)thio]-3H-1,2,3-triazolo[4,5-d]-pyrimidin-3-yl]-2-cyclopenten-1-yl]oxy]-acetic acid, ethyl ester;

[1S-(cis)] 2-[[4-[7-Amino-5-[(3,3,3-trifluoropropyl)thio]-3H-1,2,3-triazolo[4,5-d]pyrimidin-3-yl]-2-cyclopenten-1-yl]oxy]-acetic acid, ethyl ester; *or*

[1S-(cis)] 2-[[4-[7-Amino-5-[(3,3,3-trifluoropropyl)thio]-3H-1,2,3-triazolo[4,5-d]pyrimidin-3-yl]-2-cyclopenten-1-yl]oxy]-1-ethanol[;].

13. The compounds:

[3aR-(3aα,4α,6α,6aα)]-2-[6-[7-Amino-5-[(3,3,3-trifluoropropyl)thio]-3H-1,2,3-triazolo[4,5-d]-pyrimidin-3-yl]-tetrahydro-2,2-dimethyl-4H-cyclopenta-1,3-dioxol-4-yloxy]ethanol;

[3aR-(3aα,4α,6α,6aα)]-2-[6-[7-Bromo-5-[(3,3,3-trifluoropropyl)thio]-3H-1,2,3-triazolo[4,5-d]-pyrimidin-3-yl]-tetrahydro-2,2-dimethyl-4H-cyclopenta-1,3-dioxol-4-yloxy]ethanol;

[3aR-[3aα,4α,6α(1R*,2S*),6aα]-2-[6-(7-Phenylcyclopropyl)amino]-5-[(3,3,3-trifluoropropyl)thio]-3H-1,2,3-triazolo[4,5-d]pyrimidin-3-yl]-tetrahydro-2,2-dimethyl-4H-1,3-dioxol-4-yloxy]ethanol;

[3aR-[3aα,4α,6α(1R*,2S*),6aα]-6-[[7-[(3,4-Difluorophenyl)cyclopropyl]amino]-5-(propylthio)-3H-1,2,3-triazolo[4,5-d]pyrimidin-3-yl]-tetrahydro-2,2-dimethyl-4H-cyclopenta-1,3-dioxol-4-ol;

[3aR-[3aα,4α,6α(1R*,2S*),6aα]]-6-[[7-[(3,4-Difluorophenyl)cyclopropyl]amino]-5-(propylsulfonyl)-3H-1,2,3-triazolo[4,5-d]pyrimidin-3-yl]-tetrahydro-2,2-dimethyl-4H-cyclopenta-1,3-dioxol-4-ol;

[3aR-[3aα,4α,6α(1R*,2S*),6aα]]-6-[5-(Butylthio)-7-[[2-(3,4-difluorophenyl)cyclopropyl]amino]-3H-1,2,3-triazolo[4,5-d]pyrimidin-3-yl]-tetrahydro-2,2-dimethyl-4H-cyclopenta-1,3-dioxol-4-ol;

[3aR-[3aα,4α,6α(1R*,2S*),6aα]]-2-[6-[[5-(Butylthio)-7-chloro-3H-1,2,3-triazolo[4,5-d]pyrimidin-3-yl]-tetrahydro-2,2-dimethyl-4H-cyclopenta-1,3-dioxol-4-yl]oxy]-ethanol; *or*

[3aR-[3aα,4α,6aα(1R*,2S*),6aα]]-2-[6-[[5-(Butylthio)-7-[2-phenylcyclopropyl]amino-3H-1,2,3-triazolo[4,5-d]pyrimidin-3-yl]-tetrahydro-2,2-dimethyl-4H-cyclopenta-1,3-dioxol-4-yl]oxy]-ethanol[;].

14. A method of treatment of stroke which comprises administering to a person suffering therefrom a therapeutically effective amount of the compound according to claim 1.

15. A compound chosen from:

[1R-[1α,2α,3β(1R*,2S*),5β]]-3-[7-[[2-(4-Fluorophenyl)cyclopropyl]amino]-5-[(3,3,3-trifluoropropyl)thio]-3H-1,2,3-triazolo[4,5-d]pyrimidin-3-yl]-5-(hydroxymethyl)-cyclopentane-1,2-diol;

[1R-[1α,2α,3β(1R*,2S*),5β]]-3-[7-[[2-(3,4-Difluorophenyl)cyclopropyl]amino]-5-[(3,3,3-trifluoropropyl)thio]-3H-1,2,3-triazolo[4,5-d]pyrimidin-3-yl]-5-(hydroxymethyl)-cyclopentane-1,2-diol;

[1S-[1α,2α,3β(1S*,2R*),5β]]-3-[7-[[2-(3,4-Difluorophenyl)cyclopropyl]amino]-5-(propylthio)-3H-1,2,3-triazolo[4,5-d]pyrimidin-3-yl]-5-(2-hydroxyethoxy)-cyclopentane-1,2-diol;

1R-[1α,2α,3β(1R*,2S*)5β]]-3-[5-(Butylthio)-7-[[2-(3,4-difluorophenyl)cyclopropyl]amino]-3H-1,2,3-triazolo[4,5-d]pyrimidin-3-yl]-5-(hydroxymethyl)-cyclopentane-1,2-diol;

[1S-[1α,2β,3β,4α(1S*,2R*)]]-4-[5-(Butylthio)-7-[[2-(4-fluorophenyl)cyclopropyl]amino]-3H-1,2,3-triazolo[4,5-d]pyrimidin-3-yl]-cyclopentane-1,2,3-triol; and pharmaceutically acceptable salts and solvates thereof, and solvates of such salts.

16. A compound chosen from:

[1R-[1α,2α,3β(1R*,2S*),5β]]-3-[7-[[2-(4-Fluorophenyl)cyclopropyl]amino]-5-[(3,3,3-trifluoropropyl)thio]-3H-1,2,3-triazolo[4,5-d]pyrimidin-3-yl]-5-(hydroxymethyl)-cyclopentane-1,2-diol;

[1R-[1α,2α,3β(1R*,2S*),5β]]-3-[7-[[2-(3,4-Difluorophenyl)cyclopropyl]amino]-5-[(3,3,3-trifluoropropyl)thio]-3H-1,2,3-triazolo[4,5-d]pyrimidin-3-yl]-5-(hydroxymethyl)-cyclopentane-1,2-diol;

[1S-[1α,2α,3β(1S*,2R*),5β]]-3-[7-[[2-(3,4-Difluorophenyl)cyclopropyl]amino]-5-(propylthio)-3H-1,2,3-triazolo[4,5-d]pyrimidin-3-yl]-5-(2-hydroxyethoxy)-cyclopentane-1,2-diol;

1R-[1α,2α,3β(1R*,2S*),5β]]-3-[5-(Butylthio)-7-[[2-(3,4-difluorophenyl)cyclopropyl]amino]-3H-1,2,3-triazolo[4,5-d]pyrimidin-3-yl]-5-(hydroxymethyl)-cyclopentane-1,2-diol; and

[1S-[1α,2β,3β,4α(1S*,2R*)]]-4-[5-(Butylthio)-7-[[2-(4-fluorophenyl)cyclopropyl]amino]-3H-1,2,3-triazolo[4,5-d]pyrimidin-3-yl]-cyclopentane-1,2,3-triol.

17. A compound chosen from:

[1R-[1α,2α,3β(1R*,2S*),5β]]-3-[7-[[2-(3,4-Difluorophenyl)cyclopropyl]amino]-5-[(3,3,3-trifluoropropyl)thio]-3H-1,2,3-triazolo[4,5-d]pyrimidin-3-yl]-5-(hydroxymethyl)-cyclopentane-1,2-diol;

[1S-[1α,2α,3β(1S*,2R*),5β]]-3-[7-[[2-(3,4-Difluorophenyl)cyclopropyl]amino]-5-(propylthio)-3H-1,2,3-triazolo[4,5-d]pyrimidin-3-yl]-5-(2-hydroxyethoxy)-cyclopentane-1,2-diol; and pharmaceutically acceptable salts and solvates thereof, and solvates of such salts.

18. A compound chosen from:

[1R-[1α,2α,3β(1R*,2S*)5,β]]-3-[7-[[2-(3,4-Difluorophenyl)cyclopropyl]amino]-5-[(3,3,3-trifluoropropyl)thio]-3H-1,2,3-triazolo[4,5-d]pyrimidin-3-yl]-5-(hydroxymethyl)-cyclopentane-1,2-diol; and

[1S-[1α,2α,3β(1S*,2R*),5β]]-3-[7-[[2-(3,4-Difluorophenyl)cyclopropyl]amino]-5-(propylthio)-3H-1,2,3-triazolo[4,5-d]pyrimidin-3-yl]-5-(2-hydroxyethoxy)-cyclopentane-1,2-diol.

19. An oral pharmaceutical composition comprising

[1S-[1α,2α,3β(1S*,2R*),5β]]-3-[7-[[2-(3,4-Difluorophenyl)cyclopropyl]amino]-5-(propylthio)-3H-1,2,3-triazolo[4,5-d]pyrimidin-3-yl]-5-(2-hydroxyethoxy)-cyclopentane-1,2-diol in combination with a pharmaceutically acceptable diluent, adjuvant, and/or carrier suitable for oral administration, wherein said oral pharmaceutical composition is in the form of a tablet, pill, capsule, liquid, powder, or granule.

20. The oral pharmaceutical composition according to claim 19, wherein said oral pharmaceutical composition is in the form of a tablet.

21. The oral pharmaceutical composition according to claim 19, wherein said liquid is a syrup or suspension.

22. A method of treatment of post-myocardial infarction which comprises orally administering to a patient suffering therefrom a therapeutically effective amount of [1S-[1α,2α,3β(1S*,2R*),5β]]-3-[7-[[2-(3,4-Difluorophenyl)cyclopropyl]amino]-5-(propylthio)-3H-1,2,3-triazolo[4,5-d]pyrimidin-3-yl]-5-(2-hydroxyethoxy)-cyclopentane-1,2-diol.

23. A method of treatment of stroke which comprises orally administering to a person suffering therefrom a therapeutically effective amount of [1S-[1α,2α,3β(1S*,2R*),5β]]-3-[7-[[2-(3,4-Difluorophenyl)cyclopropyl]amino]-5-(propylthio)-3H-1,2,3-triazolo[4,5-d]pyrimidin-3-yl]-5-(2-hydroxyethoxy)-cyclopentane-1,2-diol.

* * * * *